(12) United States Patent
Barr et al.

(10) Patent No.: US 10,837,031 B2
(45) Date of Patent: Nov. 17, 2020

(54) RECOMBINANT PRODUCTION SYSTEMS FOR PRENYLATED POLYKETIDES OF THE CANNABINOID FAMILY

(71) Applicant: BayMedica, Inc., Incline Village, NV (US)

(72) Inventors: Philip J. Barr, Oakland, CA (US); Charles K. Marlowe, Emerald Hills, CA (US); Jianping Sun, Redwood City, CA (US)

(73) Assignee: BAYMEDICA, INC., Incline Village, NV (US)

( * ) Notice: Subject to any disclaimer, the term of this patent is extended or adjusted under 35 U.S.C. 154(b) by 0 days.

(21) Appl. No.: 15/976,755

(22) Filed: May 10, 2018

(65) Prior Publication Data

US 2018/0334692 A1 Nov. 22, 2018

Related U.S. Application Data

(60) Provisional application No. 62/504,456, filed on May 10, 2017.

(51) Int. Cl.
| | |
|---|---|
| C12P 7/42 | (2006.01) |
| C12N 1/15 | (2006.01) |
| C12N 9/88 | (2006.01) |
| C12N 9/00 | (2006.01) |

(52) U.S. Cl.
CPC ............... *C12P 7/42* (2013.01); *C12N 9/88* (2013.01); *C12N 9/93* (2013.01); *C12Y 404/01026* (2015.07); *C12Y 602/01* (2013.01)

(58) Field of Classification Search
None
See application file for complete search history.

(56) References Cited

U.S. PATENT DOCUMENTS

| | | | |
|---|---|---|---|
| 3,919,322 | A | 11/1975 | Brossi et al. |
| 5,824,485 | A | 10/1998 | Thompson et al. |
| 5,919,651 | A | 7/1999 | Hitzeman et al. |
| 6,033,883 | A | 3/2000 | Barr et al. |
| 6,228,647 | B1 | 5/2001 | Voytas et al. |
| 6,258,566 | B1 | 7/2001 | Barr et al. |
| 7,078,233 | B2 | 7/2006 | Barr et al. |
| 8,124,390 | B2 | 2/2012 | Kuzuyama et al. |

(Continued)

FOREIGN PATENT DOCUMENTS

| | | |
|---|---|---|
| WO | 2017161041 | 9/2017 |
| WO | 2018/200888 A1 | 11/2018 |
| WO | 2019/071000 A1 | 4/2019 |

OTHER PUBLICATIONS

Pamplaniyil, K., "Identification, isolation and functional characterization of prenyltransferases in *Cannabis sativa* L.", Jan. 1, 2018; Technischen Universität Dortmund; PhD dissertation; https://eldorado.tu-dortmund.de/handle/2003/36335; 141 pages.

(Continued)

*Primary Examiner* — Rebecca E Prouty
(74) *Attorney, Agent, or Firm* — Kilpatrick, Townsend & Stockton, LLP

(57) ABSTRACT

The present invention relates generally to production methods, enzymes and recombinant yeast strains for the biosynthesis of clinically important prenylated polyketides of the cannabinoid family. Using readily available starting materials, heterologous enzymes are used to direct cannabinoid biosynthesis in yeast.

13 Claims, 6 Drawing Sheets

Specification includes a Sequence Listing.

(56) References Cited

U.S. PATENT DOCUMENTS

| | | | |
|---|---|---|---|
| 8,236,552 | B2 | 8/2012 | Millis et al. |
| 8,476,049 | B2 | 7/2013 | McAuliffe et al. |
| 8,884,100 | B2 | 11/2014 | Page et al. |
| 9,169,496 | B2 | 10/2015 | Marliere |
| 9,546,362 | B2 | 1/2017 | Page et al. |
| 9,611,460 | B2 | 4/2017 | Page et al. |
| 9,637,763 | B2 | 5/2017 | Barr |
| 2014/0141476 | A1 | 5/2014 | Page et al. |
| 2015/0299732 | A1 | 10/2015 | Millis et al. |
| 2015/0336874 | A1 | 11/2015 | Koch et al. |
| 2016/0010126 | A1 | 1/2016 | Poulos et al. |
| 2016/0068869 | A1 | 3/2016 | Piotrowski et al. |

OTHER PUBLICATIONS

Baek SH et al. (1985) "Boron trifluoride etherate on alumina—a modified Lewis acid reagent. An improved synthesis of cannabinol." *Tetrahedron Letters* 26(8): 1083-1086.

Black PN, et al. (May 16, 2006) "Yeast acyl-CoA synthetases at the crossroads of fatty acid metabolism and regulation." *Biochim Biophys Acta.* 1771(3):286-98.

Crombie L, et al. (Jan. 1, 1988) "Synthesis of Cannabinoids Carrying ω-Carboxy Substituents: The Cannabidiols, Cannabinol and Δ1- and Δ6-Tetrahydrocannabinols of this Series." *J. Chem. Soc. Perkin Trans. I* 1998: 1255-1262.

Dellas N, et al. (Apr. 14, 2010) "Mutation of Archaeal Isopentenyl Phosphate Kinase Highlights Mechanism and Guides Phosphorylation of Additional Isoprenoid Monophosphates." *ACS Chemical Biology* 5(6):589-601.

Elsohly M, et al (2005) "Chemical constituents of marijuana: The complex mixture of natural cannabinoids." *Life Sciences* 78: 539-548.

Fellermeier M, et al. (May 8, 1998) "Prenylation of olivetolate by a hemp transferase yields cannabigerolic acid, the precursor of tetrahydrocannabinol." *FEBS Lett* 427: 283-285.

Fitzpatrick AH, et al. (Apr. 12, 2011) "Farnesol kinase is involved in farnesol metabolism, ABA signaling and flower development in *Arabidopsis.*" *The Plant Journal* (2011) (66), 1078-1088.

Flores-Sanchez I, et al. (Apr. 8, 2008) "Secondary metabolism in cannabis." *Phytochem Rev* 7:615-639.

Flores-Sanchez I (Oct. 29, 2008) "Polyketide synthases in *Cannabis sativa* L." Doctoral thesis, Leiden University.

Flores-Sanchez I, et al. (Dec. 3, 2008) "PKS Activities and Biosynthesis of Cannabinoids and Flavonoids in *Cannabis sativa* L. Plants." *Plant Cell Physiol.* 49(12):1767-1782.

Gagne S et al. (Jul. 31, 2012) "Identification of olivetolic acid cyclase from Cannabis sativa reveals a unique catalytic route to plant polyketides." *Proc. Nat. Acad. Sci.* USA 109: 12811-12816.

Hazekamp A et al. (2005) "Chromatographic and Spectroscopic Data of Cannabinoids from *Cannabis sativa* L." *Journal of Liquid Chromatography & Related Techniques* 28: 2361-2382.

Kage H, et al. (Oct. 28, 2015) "Chemical chain termination resolves the timing of ketoreduction in a partially reducing iterative type I polyketide synthase." *Org. Biomol. Chem.* 13: 11414-11417.

Kealey JT, et al. (Jan. 20, 1998). "Production of a polyketide natural product in nonpolyketide-producing prokaryotic and eukaryotic hosts." *Proc. Nat. Acad. Sci.* USA 95 (2) 505-509.

Kumano T, et al. (Sep. 1, 2008) "Chemoenzymatic syntheses of prenylated aromatic small molecules using *Streptomyces* prenyltransferases with relaxed substrate specificities." *Bioorg Med Chem.* 16(17): 8117-8126.

Kulkarni R, et al. (Jul. 16, 2013) "Characterization of three novel isoprenyl diphosphate synthases from the terpenoid rich mango fruit." *Plant Physiology and Biochemistry* 71: 121-131.

Kuzuyama T, et al. (Jun. 16, 2005) "Structural basis for the promiscuous biosynthetic prenylation of aromatic natural products." *Nature* 435(7044): 983-987.

Li, M. et al. (Sep. 4, 2015) "*De novo* production of resveratrol from glucose or ethanol by engineered *Saccharomyces cerevisiae*." Metabolic Engineering 32 (2015) 1-11.

Liu Y, et al. (Apr. 7, 2016) "Improving the catalytic activity of isopentenyl phosphate kinase through protein coevolution analysis." *Scientific Reports* 6:24117, 7 pages.

Mabanglo M, et al. (Jul. 20, 2012) "Mutagenesis of Isopentenyl Phosphate Kinase to Enhance Geranyl Phosphate Kinase Activity."

Mechoulam R, et al. (1969) "Stereoselective synthesis of cannabinoid 1,5 dienes." *Tetrahedron Letters* 60:5349-5352.

Miyazawa T, et al. (Sep. 16, 2015) "Identification of Middle Chain Fatty Acyl-CoA Ligase Responsible for the Biosynthesis of 2-Alkylmalonyl-CoAs for Polyketide Extender Unit." *J. Biol. Chem.* 290: 26994-27011.

Morimoto S, et al. (Nov. 20, 1998) "Purification and characterization of cannabichromenic acid synthase from Cannabis sativa." *Phytochemistry* 49: 1525-1529.

Morimoto S, et al. (1999) "Biosynthesis of cannabinoids in *Cannabis sativa* L." *Curr Top Phytochem* 2: 103-113.

Porwoll J, et al (1985) "Synthesis of [5,6-$^{13}C_2$,1-$^{14}C$]olivetolic acid, methyl [1'-$^{13}C$]olivetolate and [5,6-$^{13}C_2$,1-$^{14}C$]cannabigerolic acid." *Journal of Labelled Compounds and Radiopharmaceuticals.* 22(3): 257-271.

Shockey J, et al. (Jun. 2003) "*Arabadopsis* Contains a Large Superfamily of Acyl-Activating Enzymes. Phylogenetic and Biochemical Analysis Reveals a New Class of Acyl-Coenzyme A Synthetases." *Plant Physiology* 132: 1065-1076.

Shockey J, et al. (Mar. 28, 2011) "Genome-level and biochemical diversity of the acyl-activating enzyme superfamily in plants." *The Plant Journal* 66: 143-160.

Shoyama Y, et al. (1978) "Cannabis XI. Synthesis of cannabigerorcinic-carboxyl-$^{14}C$ acid, cannabigerovarinic carboxyl-$^{14}C$ acid, cannabidivarinic-carboxyl-$^{14}C$ acid and dl-cannabichromevarinic-carboxyl-$^{14}C$ acid." *Journal of Labelled Compounds and Radiopharmaceuticals.* 14(8):835-842.

Sirikantaramas S, et al. (2017) "Chapter 8. Cannabinoids: Biosynthesis and Biotechnological Applications." *Cannabis sativa* L.—*Botany and Biotechnology*, S. Chandra et al. (eds.), Springer International Publishing AG, pp. 183-206.

Stout JM et al. (Jun. 1, 2012) "The hexanoyl-CoA precursor for cannabinoid biosynthesis is formed by an acyl-activating enzyme in Cannabis sativa trichomes." *The Plant Journal* 71:353-365.

Taura F, et al. (Jun. 26, 2007) "Cannabidiolic-acid synthase, the chemotype-determining enzyme in the fiber-type Cannabis sativa." *FEBS Lett* 581: 2929-2934.

Taura F, et al. (Jun. 18, 2009) "Characterization of olivetol synthase, a polyketide synthase putatively involved in cannabinoid biosynthetic pathway." *FEBS Lett* 583: 2061-2066.

Van Bakel H et al. (Oct. 20, 2011) "The draft genome and transcriptome of Cannabis sativa." *Genome Biology* 12: R102.

Wang CH et al. (May 23, 2016) "Characterization and Functional Analysis of 4-Coumarate:CoA Ligase Genes in Mulberry" *PLos ONE* 11(5): e0155814.

Wong J et al. (Jan. 2017) "Microbial Production of Isoprenoids." *Consequences of Microbial Interactions with Hydrocarbons, Oils, and Lipids: Production of Fuels and Chemicals, Handbook of Hydrocarbon and Lipid Microbiology* S.Y. Lee (ed.) Springer International Publishing; 24 pages.

Yang X, et al. (Jan. 18, 2016) "Structural basis for olivetolic acid formation by a polyketide cyclase from *Cannabis sativa."* FEBS J. 283:1088-1106.

PCT/US2018/032155, "International Search Report and Written Opinion", dated Sep. 25, 2018, 21 pages.

Taura et al., "Purification and Characterization of Cannabidiolic-acid Synthase from *Cannabis sativa* L.", Journal of Biological Chemistry, vol. 271,No. 29, Jul. 19, 1996, pp. 17411-17416.

Cannabichromanone
R3: C3 or C5 side chain

Cannabicoumaronone

Cannabicitran 10-oxo-$\Delta^{6a(10a)}$-Tetrahydrocannabinol (OTHC)

Cannabiglendol $\Delta^7$-Isotetrahydrocannabinol
R3: C3 or C5

RECOMBINANT PRODUCTION SYSTEMS FOR PRENYLATED POLYKETIDES OF THE CANNABINOID FAMILY

CROSS-REFERENCES TO RELATED APPLICATIONS

This application claims benefit of U.S. Provisional Application No. 62/504,456, filed May 10, 2017, which is herein incorporated by reference for all purposes.

REFERENCE TO A "SEQUENCE LISTING" SUBMITTED AS ASCII TEXT FILES VIA EFS WEB

The Sequence Listing written in file SEQ_104059-1087398.txt created on Aug. 3, 2018, 27,445 bytes, machine format IBM-PC, MS-Windows operating system, in accordance with 37 C.F.R. §§ 1.821 to 1.825, is hereby incorporated by reference in its entirety for all purposes.

FIELD OF THE INVENTION

The present invention relates generally to production methods, enzymes and recombinant host strains, e.g., yeast strains, for the biosynthesis of clinically important prenylated polyketides of the cannabinoid family. Using readily available starting materials, heterologous enzymes are used to direct cannabinoid biosynthesis in eukaryotic microorganisms, e.g., yeast.

BACKGROUND OF THE INVENTION

*Cannabis sativa* varieties have been cultivated and utilized extensively throughout the world for a number of applications. Stems, branches, and leaves are used in fibers and fiber-based products; sprouts and seeds as food; seeds for inexpensive oils; flowers for aromatic, recreational, ritual and medicinal purposes; and flowers and roots for nutritional and additional medicinal and pharmaceutical applications. Indeed, many controlled clinical studies and anecdotal or open-label studies in humans have been documented that demonstrate beneficial effects of both plant extracts and purified *C. sativa* plant compounds in many human medical conditions. Beneficial activities of the cannabinoid family of compounds described from human studies range from neurological to mood/behavior disorders, and to gastrointestinal disorders as well as sleeping, appetite and fatigue problems. Other uses or potential uses include the treatment of various microbial and viral infections and the treatment of a number of cancers. Thus, as a direct result of this burgeoning list of human therapeutic indications, there currently exists an unfulfilled need for the production of pharmaceutical grade cannabinoids using sustainable, modern biopharmaceutical preparation methods.

Currently, the cannabinoids are isolated primarily via the cultivation of large acreages of *cannabis* or hemp plants in agricultural operations throughout the world, with a lower, albeit clinically important level of production methodologies that involve synthetic chemical processes. The former techniques are costly, utilize large quantities of natural resources, such as arable land and water and invariably lead to final pharmaceutical products that contain additional active cannabinoids that contaminate the desired active drug substances. This can lead to an inconsistency in the activities of the desired pure compounds leading to spurious activities in both clinical trial situations and in marketed products. Furthermore, the contamination of natural plant-derived cannabinoid preparations by toxic metals and pesticides is a problem that currently is in need of a solution. Also, because of the complex stereochemistry of many of the cannabinoids, chemical synthesis is a difficult, expensive and low-yielding process. Furthermore, the synthetic chemical production of a number of cannabinoids has been reported to produce less pharmacologically active molecules than those extracted from the *C. sativa* plant.

Synthetic biology, however, whereby products of interest are biosynthesized using isolated genetic pathways in engineered microorganisms, offers potential solutions to the large-scale commercial manufacture issues of many naturally occurring compounds.

The first chemical building blocks of the cannabinoid molecules and their analogs are polyketides that are derived in nature from a type III polyketide synthase (PKS). For a detailed description of PKSs in *C. sativa*, see Flores Sanchez, I. J., 2008, Doctoral thesis, Leiden University and Sanchez and Verpoorte, Phytochem Rev (2008) 7:615-639.

Polyketides generally are synthesized by condensation of two-carbon units in a manner analogous to fatty acid synthesis. In general, the synthesis involves a starter unit and extender units; these starter units are derived from, for example, acylthioesters, typically acetyl-, coumaroyl-, propionyl-, malonyl- or methylmalonyl-coenzyme-A (CoA) thioesters. The first enzymatic step in the biosynthesis of the more prevalent cannabinoids, however, is the formation of olivetolic acid by a type III PKS enzyme that catalyzes the condensation of hexanoyl-CoA with three molecules of malonyl-CoA to form a tetraketide that is then cyclized and aromatized by a separate gene-encoded cyclase enzyme. The major cannabinoids, including Δ9-tetrahydrocannabinolic acid and cannabidiolic acid, are thus formed from the initiating precursor hexanoyl-CoA, a medium chain fatty acyl-CoA. Other, less prevalent cannabinoids with variant side-chains are formed from aliphatic-CoAs of different lengths (e.g., Δ9-tetrahydrocannabivarinic acid is formed from an n-butanoyl-CoA starter unit). Several additional and related analogs are found in nature, and others have been chemically synthesized.

Type I and many type III iterative PKSs are enzymes with sites that are used repeatedly to reach the final polyketide product, with certain type III PKSs, including OA synthase, also requiring the action of a cyclase enzyme to catalyze effecting the final steps, namely cyclization, dehydration and aromatization of the linear tetraketide precursor.

The next steps in the natural biosynthetic pathway to the major cannabinoids involve prenylation of olivetolic acid or an olivetolic acid analog (e.g., a 2-alkyl-4,6-dihydroxybenzoic acid), wherein a 10-carbon geranyl-diphosphate is condensed by the prenylase geranyl-diphosphate:olivetolate geranyl transferase (GOT) (Fellermeier and Zenk, 1998) to yield cannabigerolic acid (CBGA); which is further oxido-cyclized, for example, into CBDA, Δ9-THCA and CBCA (Morimoto et al., 1999) by the enzymes cannabidiolic acid synthase (Taura et al., 2007), Δ9-tetrahydrocannabinolic acid synthase (Sirikantaramas et al., 2004) and cannabichromenic acid synthase (Morimoto et al., 1998), respectively.

BRIEF SUMMARY OF THE INVENTION

Provided herein are modified recombinant host cells, yeast strains, engineered for cannabinoid expression. In some embodiments, the host cells are genetically modified to express an exogenous polynucleotide that encodes an acyl-CoA synthetase that converts an aliphatic carboxylic acid to an acyl CoA thioester, e.g., wherein the acyl-CoA synthetase is a revS polypeptide or a CsAAE3 polypeptide; an exogenous polynucleotide that encodes olivetolic acid synthase, (iii) and an exogenous polynucleotide that encodes a 2-alkyl-4,6-dihydroxybenzoic acid cyclase (e.g., olivetolic acid cyclase). Such a host cell may also be genetically modified to express a prenyltransferase that catalyzes coupling of geranyl-pyrophosphate to olivetolic acid or an olivetolic acid analog (e.g., a 2-alkyl-4,6-dihydroxybenzoic acid) to form a cannabinoid compound.

Also provided herein are recombinant host cells genetically modified to express exogenous polynucleotides that encodes prenol and isoprenol kinase; an exogenous polynucleotide that encodes a kinase to produce dimethylallyl pyrophosphate and isopentenyl pyrophosphate when grown in the presence of exogenous prenol and isoprenol; and an exogenous polynucleotide that encodes a geranyl-pyrophosphate synthase. In some embodiments, the host cell is additionally genetically modified to express an exogenous polynucleotide that encodes a prenyltransferase that catalyzes coupling of geranyl-pyrophosphate to olivetolic acid or an olivetolic acid analog (e.g., a 2-alkyl-4,6-dihydroxybenzoic acid) to form a cannabinoid compound.

Also provided herein are methods for producing cannabinoid products. The methods include: culturing a modified recombinant host cell containing an exogenous polynucleotide that encodes an acyl-CoA synthetase that converts an aliphatic carboxylic acid to an acyl CoA thioester; an exogenous polynucleotide that encodes olivetolic acid synthase that produces a tetraketide from an Acyl-CoA and malonyl CoA; and an exogenous polynucleotide that encodes a 2-alkyl-4,6-dihydroxybenzoic acid cyclase (e.g., olivetolic acid cyclase); under conditions in which products encoded by the exogenous polynucleotides are expressed and a 2-alkyl-4,6-dihydroxybenzoic acid (e.g., olivetolic acid) is produced; and converting the 2-alkyl-4,6-dihydroxybenzoic acid to the cannabinoid. The conversion can be conducted chemically or enzymatically, in vitro or in vivo.

DETAILED DESCRIPTION OF THE INVENTION

I. Introduction

Figure 1:
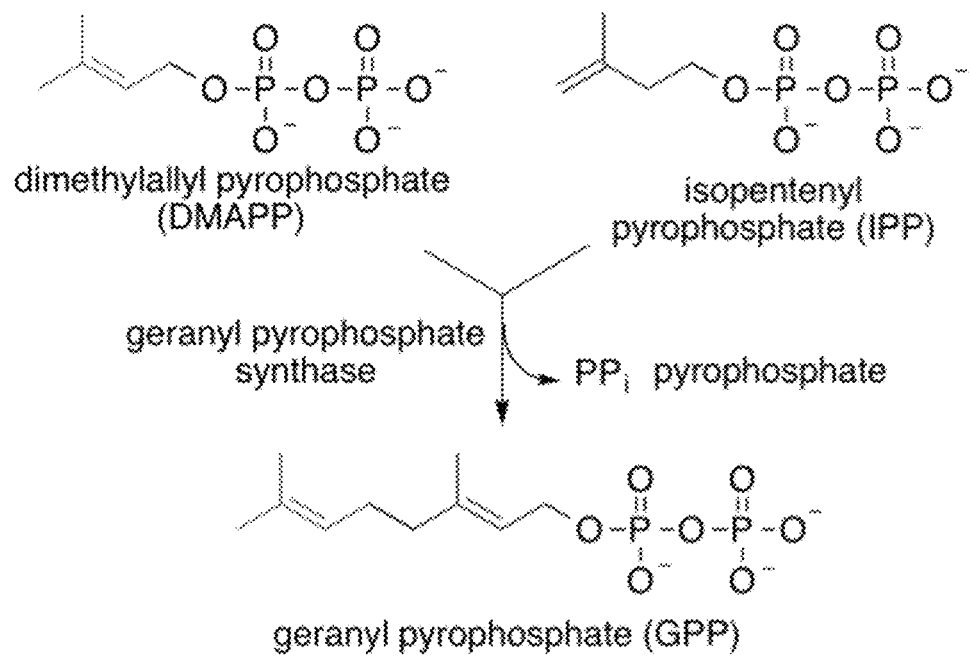
FIG. 1 depicts the biosynthetic pathway to geranyl-pyrophosphate via the pyrophosphates of prenol (dimethylallyl alcohol) and isoprenol (isopentenyl alcohol). Geranyl-pyrophosphate is the substrate for prenylation of the polyketide olivetolic acid and its analogs to form cannabigerolic acid (CBGA) and its analogs.

The present invention provides methods and materials for producing cannabinoid compounds of interest in a rapid, inexpensive and efficient manner. As such, the present invention meets a number of commercial and pharmaceutical industrial needs.

In one aspect, the present invention provides novel systems for the efficient production of the prenylated polyketides (Page, J. E., and Nagel, J. (2006). Biosynthesis of terpenophenolics in hop and *cannabis*. In Integrative Plant Biochemistry, J. T. Romeo, ed, (Oxford, UK: Elsevier), pp. 179-210), that comprise the cannabinoid family along with cannabinoid precursor molecules and their analogs, using commercial yeast biopharmaceutical manufacturing systems. In some embodiments, the yeast strains chosen as hosts belong to the *Saccharomyces cerevisiae* species of yeast that does not produce such molecules naturally. Other species of yeasts that may be employed include, but are not limited to, *Kluyveromyces lactis, K. marxianus, Pichiapastoris, Yarrowia lipolytica*, and *Hansenula polymorpha*. Similarly, filamentous fungi species, such as certain *Aspergillus* species, may also be engineered for cannabinoid production.

The present invention can employ coding sequences from both type I PKSs and type II PKSs, but in typical embodiments, the PKSs employed are from the type III class of PKS, e.g., the natural aromatic olivetolic acid synthase/cyclase systems, or the related type III orsellinic acid synthases, or modified versions of these enzymes. Genes encoding polypeptide components of type I PKSs have been used for the microbiological production of similar polyketides in heterologous microorganisms such as yeast and *E. coli*. See for example U.S. Pat. Nos. 6,033,883, 6,258,566, 7,078,233 and 9,637,763 and Kealey et al., Proc Natl Acad Sci USA (1998) 95, 505

In some embodiments, the present invention employs a process, designated multiple precursor feeding (MPF) technology, wherein a suitably modified host cell can accept and phosphorylate fed geraniol and/or 5-carbon geranyl-diphosphate precursors, along with either endogenously produced, or exogenously fed olivetolic acid or olivetolic acid analogs (e.g., 2-alkyl-4,6-dihydroxybenzoic acids) to give higher yielding cannabinoid biosynthesis than produced by de novo synthesis of all of these precursors in the same host cell. In some embodiments, geranyl-diphosphate can be generated from the two 5-carbon precursors, dimethylallyl alcohol (prenol) and isopentenyl alcohol (isoprenol) that are themselves fed and phosphorylated to the diphosphate level by suitable heterologous kinase enzymes that are engineered into the cannabinoid production strain.

II. Definitions

Unless otherwise defined, all terms of art, notations and other scientific terminology used herein are intended to have the meanings commonly understood by those of ordinary skill in the art to which the present application pertains. In some cases, terms with commonly understood meanings are defined herein for clarity and/or for ready reference, and the inclusion of such definitions herein should not necessarily be construed to represent a substantial difference over what is generally understood in the art.

As used herein, the terms "cannabinoid," "cannabinoid compound," and "cannabinoid product" are used interchangeably to refer a molecule containing a polyketide moiety, e.g., olivetolic acid or another 2-alkyl-4,6-dihydroxybenzoic acid, and a terpene-derived moiety e.g., a geranyl group. Geranyl groups are derived from the diphosphate of geraniol, known as geranyl-diphosphate or geranyl-pyrophosphate (FIG. 1) that forms the acidic cannabinoid cannabigerolic acid (CBGA). CBGA can be converted to further bioactive cannabinoids both enzymatically (e.g., by decarboxylation via enzyme treatment in vivo or in vitro to form the neutral cannabinoid cannabigerol) and chemically (e.g., by heating); see also, FIGS. 1, 2A, and 2B.

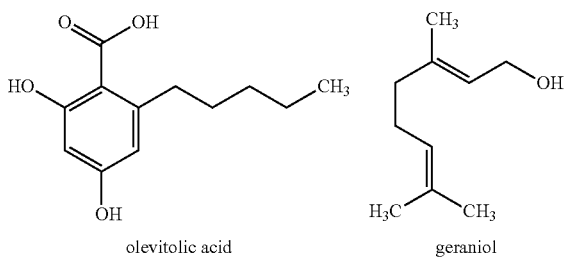 [SMILES: CCCCCc1cc(O)cc(O)c1C(=O)O ; CC(C)=CCC/C(C)=C/CO]

olevitolic acid         geraniol

The term cannabinoid includes acid cannabinoids and neutral cannabinoids. The term "acidic cannabinoid" refers to a cannabinoid having a carboxylic acid moiety. The carboxylic acid moiety may be present in protonated form (i.e., as —COOH) or in deprotonated form (i.e., as carboylate —COO⁻). Examples of acidic cannabinoids include, but are not limited to, cannabigerolic acid, cannabidiolic acid, and Δ⁹-tetrahydrocannabinolic acid. The term "neutral cannabinoid" refers to a cannabinoid that does not contain a carboxylic acid moiety (i.e., does contain a moiety —COOH or —COO⁻). Examples of neutral cannabinoids include, but are not limited to, cannabigerol, cannabidiol, and Δ⁹-tetrahydrocannabinol.

The term "2-alkyl-4,6-dihydroxybenzoic acid" refers to a compound having the structure:

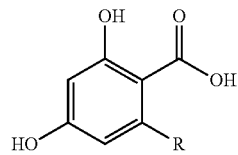

wherein R is a $C_1$-$C_{20}$ alkyl group. Examples of 2-alkyl-4,6-dihydroxybenzoic acids include, but are not limited to olivetolic acid (i.e., 2-pentyl-4,6-dihydroxybenzoic acid; CAS Registry No. 491-72-5) and divarinic acid (i.e., 2-propyl-4,6-dihydroxybenzoic acid; CAS Registry No. 4707-50-0). Olivetolic acid analogs include other 2-alkyl-4,6-dihydroxybenzoic acids and substituted resorcinols such as 5-methylresorcinol, 5-ethylresorcinol, 5-propylresorcinol, 5-hexylresorcinol, 5-heptylresorcinol, 5-octylresorcinol, and 5-nonylresorcinol.

The term "alkyl," by itself or as part of another substituent, refers to a straight or branched, saturated, aliphatic radical. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

The term "geraniol" refers to (2E)-3,7-dimethyl-2,6-octadien-1-ol (CAS Registry No. 106-24-1). The term "geranylating" refers to the covalent boding of a 3,7-dimethyl-2,6-octadien-1-yl radical to a molecule such as a 2-alkyl-4,6-hydroxybenzoic acid. Geranylation can be conducted chemically or enzymatically, as described herein.

"Organic solvent" refers to a carbon-containing substance that is liquid at ambient temperature and pressure and is substantially free of water. Examples of organic solvents include, but are not limited to, toluene, methylene chloride, ethyl acetate, acetonitrile, tetrahydrofuran, benzene, chloroform, diethyl ether, dimethyl formamide, dimethyl sulfoxide, and petroleum ether.

The term "acid" refers to a substance that is capable of donating a proton (i.e., a hydrogen cation) to form a conjugate base of the acid. Examples of acids include, but are not limited to, mineral acids (e.g., hydrochloric acid, sulfuric acid, and the like), carboxylic acids (e.g., acetic acid, formic acid, and the like), and sulfonic acids (e.g., methanesulfonic acid, p-toluenesulfonic acid, and the like).

Throughout this specification and claims, the word "comprise," or variations such as "comprises" or "comprising," will be understood to imply the inclusion of a stated integer or group of integers but not the exclusion of any other integer or group of integers.

The terms "identical" or percent "identity," in the context of two or more polypeptide sequences, refer to two or more sequences or subsequences that are the same or have a specified percentage of amino acid residues that are the same (e.g., at least 70%, at least 75%, at least 80%, 85%, 90%, 91%, 92%, 93%, 94%, 95%, 96%, 97%, 98%, 99%, or higher) identity over a specified region, when compared and aligned for maximum correspondence over a comparison window or designated region. Alignment for purposes of determining percent amino acid sequence identity can be performed in various methods, including those using publicly available computer software such as BLAST, BLAST-2, ALIGN or Megalign (DNASTAR) software.

Examples of algorithms that are suitable for determining percent sequence identity and sequence similarity the BLAST 2.0 algorithms, which are described in Altschul et al., Nuc. Acids Res. 25:3389-3402 (1977) and Altschul et al., J. Mol. Biol. 215:403-410 (1990). Thus, BLAST 2.0 can be used with the default parameters described to determine percent sequence.

A "conservative" substitution as used herein refers to a substitution of an amino acid such that charge, hydrophobicity, and/or size of the side group chain is maintained. Illustrative sets of amino acids that may be substituted for one another include (i) positively-charged amino acids Lys, Arg and His; (ii) negatively charged amino acids Glu and Asp; (iii) aromatic amino acids Phe, Tyr and Trp; (iv) nitrogen ring amino acids His and Trp; (v) large aliphatic nonpolar amino acids Val, Leu and Ile; (vi) slightly polar amino acids Met and Cys; (vii) small-side chain amino acids Ser, Thr, Asp, Asn, Gly, Ala, Glu, Gln and Pro; (viii) aliphatic amino acids Val, Leu, Ile, Met and Cys; and (ix) small hydroxyl amino acids Ser and Thr. Reference to the charge of an amino acid in this paragraph refers to the charge at physiological pH.

In specific cases, abbreviated terms are used. For example, the term "CBGA" refers to cannabigerolic acid. Likewise: "OA" refers to olivetolic acid; "CBG" refers to cannabigerol; "CBDA" refers to cannabidiolic acid; "CBD" refers to cannabidiol; "THC" refers to $\Delta^9$-tetrahydrocannabinol ($\Delta^9$-THC); "$\Delta^8$-THC" refers to $\Delta^8$-tetrahydrocannabinol; "THCA" refers to $\Delta^9$-tetrahydrocannabinolic acid ($\Delta^9$-THCA); "$\Delta^8$-THCA" refers to $\Delta^8$-tetrahydrocannabinolic acid; "CBCA" refers to cannabichromenic acid; "CBC" refers to cannabichromene; "CBN" refers to cannabinol; "CBDN" refers to cannabinodiol; "CBNA" refers to cannabinolic acid; "CBV" refers to cannabivarin; "CBVA" refers to cannabivarinic acid; "THCV" refers to $\Delta^9$-tetrahydrocannabivarin ($\Delta^9$-THCV); "$\Delta^8$-THCV" refers to "$\Delta^8$-tetrahydrocannabivarin; "THCVA" refers to $\Delta^9$-tetrahydrocannabivarinic acid ($\Delta^9$-THCV); "$\Delta^8$-THCVA" refers to $\Delta^8$-tetrahydrocannabivarinic acid; "CBGV" refers to cannabigerovarin; "CBGVA" refers to cannabigerovarinic acid; "CBCV" refers to cannabichromevarin; "CBCVA" refers to cannabichromevarinic acid; "CBDV" refers to cannabidivarin; "CBDVA" refers to cannabidivarinic acid; "MPF" refers to multiple precursor feeding; "PKS" refers to a polyketide synthase; "GOT" refers to geranyl pyrophosphate olivetolate geranyl transferase; "YAC" refers to yeast artificial chromosome; "IRES" or "internal ribosome entry site" means a specialized sequence that directly promotes ribosome binding and mRNA translation, independent of a cap structure; and "HPLC" refers to high performance liquid chromatography.

As used herein and in the appended claims, the singular forms "a," "and," and "the" include plural referents unless the context clearly dictates otherwise.

The molecular biology techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted. Before the present methods, expression systems, and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention, which will be limited only by the appended claims.

III. Cannabinoid Expression Systems

Figure 2A:
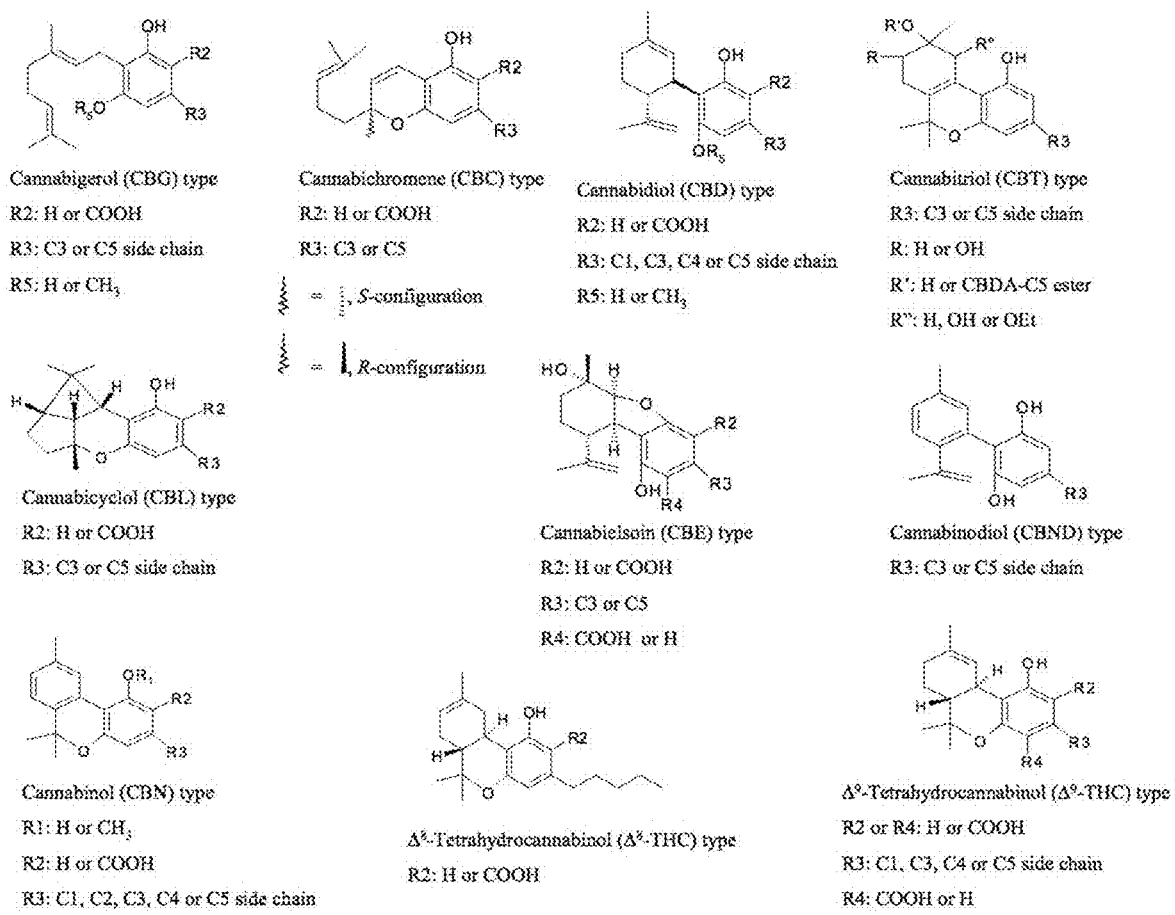
FIG. 2A depicts the chemical structures of the major cannabinoids accessible via the multiple precursor feeding (MPF) strategy (adapted from Flores Sanchez, I. J., 2008, Doctoral thesis, Leiden University, Sanchez and Verpoorte, Phytochem Rev (2008) 7:615-639).
Figure 2B:
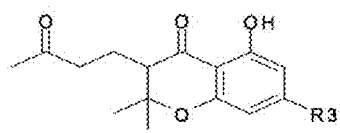
FIG. 2B depicts the chemical structures of additional cannabinoids that can be accessed using the MPF strategy together with further chemical or biochemical conversion reactions (adapted from Flores Sanchez, I. J., 2008, Doctoral thesis, Leiden University, Sanchez and Verpoorte, Phytochem Rev (2008) 7:615-639).
Figure 2B:
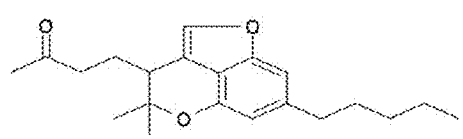
Figure 2B:
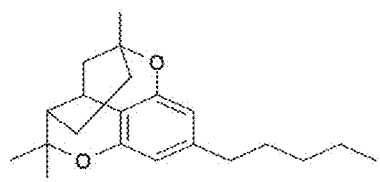
Figure 2B:
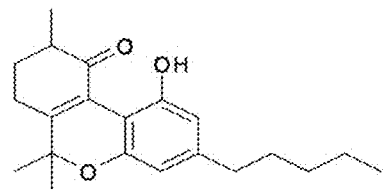
Figure 2B:
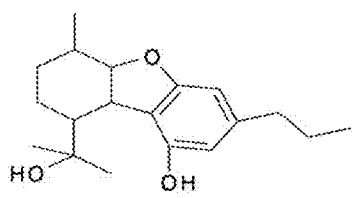
Figure 2B:
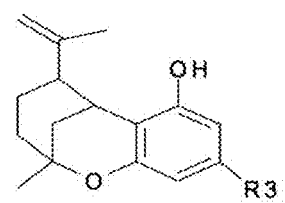
Figure 3:
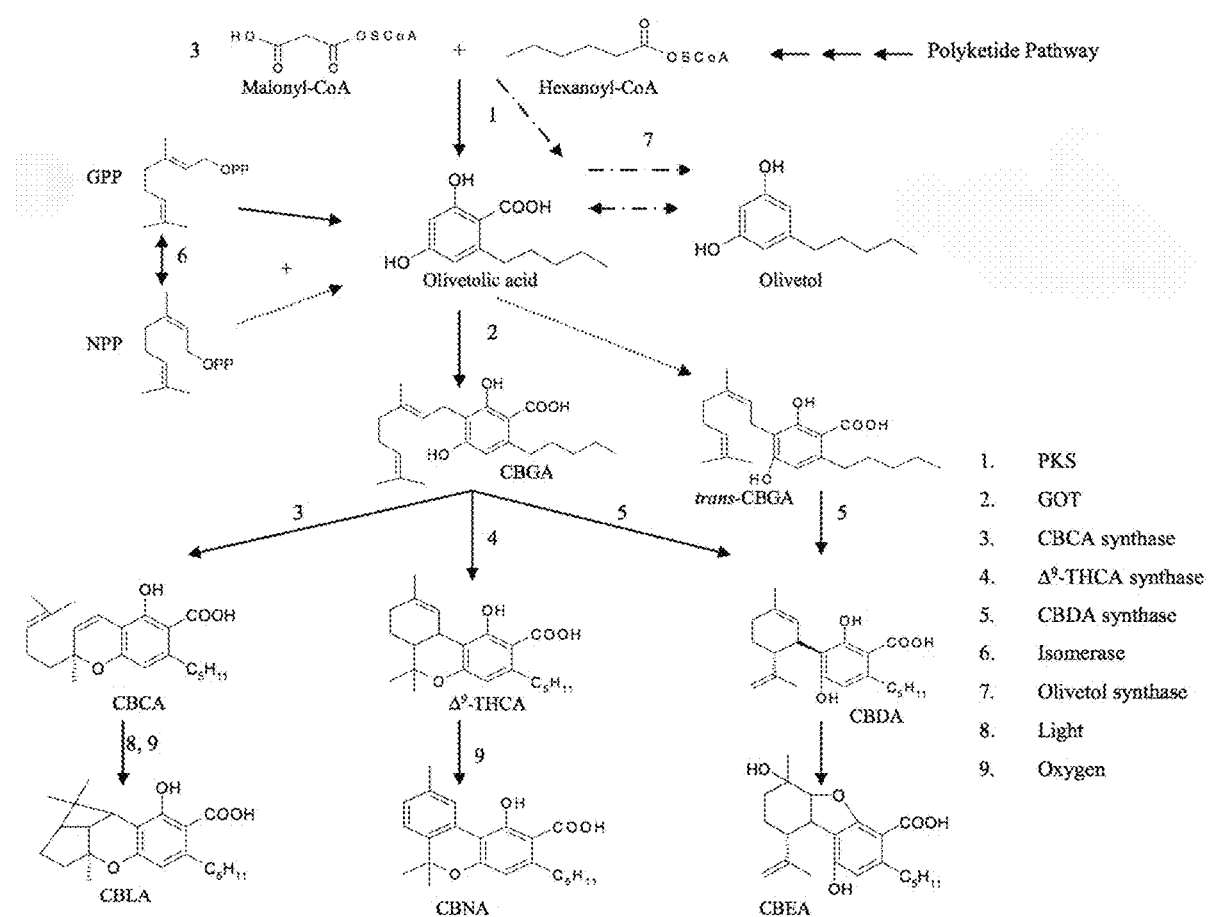
FIG. 3 depicts the overall pathway to the clinically important cannabinoid compounds that are accessible through CBGA (adapted from Flores Sanchez, I. J., 2008, Doctoral thesis, Leiden University, Sanchez and Verpoorte, Phytochem Rev (2008) 7:615-639).
Figure 4:
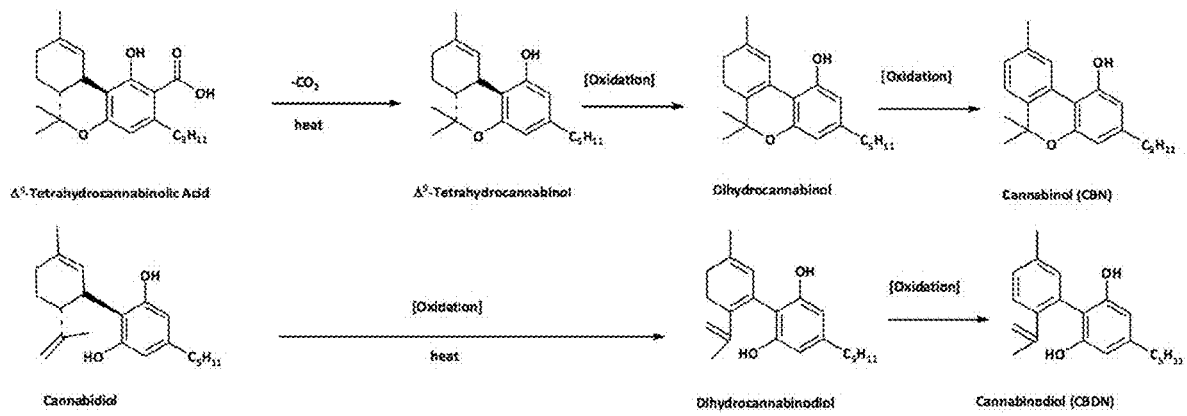
FIG. 4 depicts chemical conversions to further important cannabinoid compounds e.g., cannabinol (CBN) and cannabinodiol (CBDN), directly within yeast cells that were engineered to produce $\Delta^9$-tetrahydrocannabinolic acid ($\Delta^9$-THCA) and cannabidiol (CBD).

Cannabinoid compounds of interest include, without limitation, CBG, CBDA, CBD, THC, $\Delta^8$-THC, THCA, $\Delta^8$-THCA, CBCA, CBA, CBN, CBDN, CBNA, CBV, CBVA, THCV, THCVA, $\Delta^8$-THCA, CBGV, CBGVA, CBCV, CBCVA, CBDV and CBDVA. Given the high levels of products obtained using the novel manufacturing systems created by the present invention, also of interest are some less well-studied cannabinoids that may have more potent and selective activities in various human medical conditions. They include, without limitation, the cannabichromanones, cannabicoumaronone, cannabicitran, 10-oxo-$\Delta^{6a(10a)}$-tetrahydrohydrocannabinol (OTHC), cannabiglendol, and $\Delta^7$-isotetrahydrocannabinol, whose structures are shown in FIG. 2B.

The present invention also concerns the synthesis of cannabinoid compound intermediates. In some embodiments, the cannabinoid compound intermediate is a compound produced in one of the steps in a metabolic pathway described herein (e.g., FIG. 1 and FIG. 2A). The term "metabolic pathway" refers to a series of two or more enzymatic reactions in which the product of one enzymatic reaction becomes the substrate for the next enzymatic reaction. At each step of a metabolic pathway, intermediate compounds are formed and utilized as substrates for a subsequent step. In some embodiment, each step of the metabolic pathway occurs in a modified recombinant cell described herein. In other embodiments, at least one step of the metabolic pathway occurs in a modified recombinant cell described herein, and at least one step of the metabolic pathway occurs outside the modified recombinant cell, in the yeast media or within an additional co-cultured modified recombinant cell. The compounds produced at each step of the metabolic pathway may be called "intermediates" or "intermediate compounds" or "compound intermediates".

In one aspect, provided herein are modified recombinant host cells for cannabinoid expression. In one embodiments, the host cells are modified to express an exogenous polynucleotide that encodes an acyl-CoA synthetase that converts an aliphatic carboxylic acid to an acyl CoA thioester, e.g., a revS polypeptide, CsAAE3, or CsAAE1 polypeptide; an exogenous polynucleotide that encodes an olivetolic acid synthase, and an exogenous polynucleotide that encodes a 2-alkyl-4,6-dihydroxybenzoic acid cyclase (e.g., olivetolic acid cyclase, including embodiments in which the olivetolic acid cyclase is truncated). In some embodiments, an acyl-CoA synthetase may comprise a deletion of a transmembrane domain.

Acyl-CoA Synthetase

An "acyl-CoA synthetase", which may also be referred to herein as an "acyl-CoA synthase: an "acyl activating enzyme", or an "acyl-CoA ligase," is an enzyme that in the present invention converts an aliphatic carboxylic acid to an acyl-CoA thioester through a two-step process in which a carboxylate and ATP are converted to an enzyme-bound carboxyl-AMP intermediate (called an adenylate) with the release of pyrophosphate (PPi). The activated carbonyl carbon of the adenylate is coupled to the thiol of CoA, followed by enzyme release of the thioester and AMP. Any number of acyl-CoA synthetases can be employed in the present invention. Acyl-CoA synthetases include, but are not limited to, short-chain acyl-CoA synthetases (EC 6.2.1.1), medium chain acyl-CoA synthetases (EC 6.2.1.2), long-chain acyl-CoA synthetases (EC 6.2.1.3), and coumarate-CoA ligases (EC 6.2.1.12). Acyl-CoA synthetases typically include a 12-amino acid residue domain called the AMP-binding motif (PROSITE PS00455): [LIVMFY]-{E}-{VES}-[STG]-[STAGFG-[ST]-[STEI]-[SG]-x-[PASLIVM]-[KR] (SEQ ID NO:9). In the PROSITE sequence, each position in the sequence is separated by "-" and the symbol "x" means that any residue is accepted at the given location in the sequence. Acceptable amino acids for a given position are placed between square parentheses (e.g., [ST] indicates that serine or threonine are acceptable at the given location in the sequence), while amino acids which are not accepted at a given location are place between curly brackets (e.g., {VES} indicates that any residue except valine, glutamic acid, and serine are acceptable at the given location in the sequence). The AMP binding motif has been used to classify polypeptides as acyl activating enzymes (AAEs) and contributed to the identification of the large AAE gene superfamily present in *Arabidopsis* (Shockey et al., 2003), *Chlamydomonas reinhardtii*, *Populus trichocharpa*, and *Physcomitrella patens* (Shockey and Browse, 2011). See, e.g., Shockey et al. (*Plant Physiology*, June 2003, 132, 1065-1076; *The Plant Journal* (2011) 66: 143-160). Acyl-CoA synthetases are also described, for example, by Black et al. (*Biochim Biophys Acta.* 1771(3): 286-98, 2007); Miyazawa et al. (*J. Biol. Chem* 290 (45): 26994-27011, 2015); and Stout et al. (*Plant J.* 71(3):353-365, 2012). In some embodiments, the acyl-CoA synthetase is from an organism that biosynthesizes resveratrol. In some embodiments, the acyl-CoA synthetase is a coumarate-CoA ligase from the genus *Morus* or the genus *Vitis*. In some embodiments, the acyl-CoA synthetase is from *Ralstonia solanacearum*. In some embodiments, the acyl-CoA synthetase from *Ralstonia solanacearum* is deleted at the N-terminus, see, e.g., SEQ ID NO:8.

In some embodiments, a host cell is genetically modified to express an exogenous polynucleotide that encodes a revS polypeptide from a *Streptomyces* sp. (see, e.g., Miyazawa et al, *J. Biol. Chem.* 290:26994-27001, 2015), or variant thereof, e.g., a native homolog, ortholog or non-naturally occurring variant that has acyl-CoA synthetase activity. In some embodiments, the polynucleotide encodes a polypeptide that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO: 1. In some embodiments, the polynucleotide encodes a RevS polypeptide that has about 70%, 75%, 80%, 85%, 90%, 95%, or greater identity to the sequence set forth in SEQ ID NO:1. In some embodiments, a non-naturally occurring variant comprises one or more modifications, e.g., substitutions such as conservative substitutions, in comparison to SEQ ID NO: 1, e.g., in regions outside the AMP binding motif or catalytic site.

In some embodiments, a host cell is genetically modified to express an exogenous polynucleotide that encodes an acyl activating enzyme from *Cannabis sativa* (CsAAE3) or variant thereof, e.g., a native homolog, ortholog or non-naturally occurring variant that has acyl-CoA synthetase activity. In some embodiments, the CsAAE3 polypeptide encoded by the polynucleotide comprises an amino acid sequence that has at least about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:2. In some embodiments, the acyl-CoA synthetase polynucleotide encodes a CsAAE3, or a homolog or non-naturally occurring thereof, comprising an amino acid sequence that has about 70%, 75%, 80%, 85%, 90%, 95%, or greater identity to the sequence set forth in SEQ ID NO:2. In some embodiments, a non-naturally occurring variant comprises one or more modifications, e.g., substitutions such as conservative substitutions, in comparison to SEQ ID NO:2, e.g., in regions outside the AMP binding motif or catalytic site.

In some embodiments, a host cell is genetically modified to express an exogenous polynucleotide that encodes an acyl activating enzyme from *Cannabis sativa* (CsAAE1) or variant thereof, e.g., a native homolog, ortholog or non-naturally occurring variant that has acyl-CoA synthetase activity. In some embodiments, the CsAAE1 polypeptide encoded by the polynucleotide comprises an amino acid sequence that has at least about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:3. In some embodiments, the acyl-CoA synthetase polynucleotide encodes a CsAAE1, or a homolog thereof, comprising an amino acid sequence that has about 70%, 75%, 80%, 85%, 90%, 95%, or greater identity to the sequence set forth in SEQ ID NO:3. In some embodiments, the CsAAE1 polynucleotide encodes a polypeptide from which the transmembrane domain is deleted. In some embodiments, a non-naturally occurring variant comprises one or more modifications, e.g., substitutions such as conservative substitutions, in comparison to SEQ ID NO:3, e.g., in regions outside the AMP binding motif or catalytic site.

The acyl-CoA synthetase can be used in conjunction with a number of aliphatic carboxylic acid starting materials including, but not limited to, butanoic acid (butyric acid), pentanoic acid (valeric acid), hexanoic acid (caproic acid), heptanoic acid (enanthic acid), and octanoic acid (caprylic acid). In some embodiments, hexanoic acid is used for formation of hexanoyl-CoA by the acyl-CoA synthetase.

Olivetolic Acid Synthase

In some embodiments, a host cell is additionally genetically modified to express an exogenous polynucleotide that encodes olivetolic acid synthase or variant thereof e.g., a native homolog or ortholog, or a non-naturally occurring variant that has polyketide synthase activity. Olivetolic acid synthase (Taura et al. *FEBS Letters* 583:2061-2066, 2009), also referred to as 3, 5, 7, -trioxododecanoyl-CoA synthase, UniProtKB-B1Q2B6, is a type III PKS that that catalyzes the condensation of acyl-CoAs with three molecules of malonyl-CoA to form a 3,5,7-trioxoalkanoyl-CoA tetraketide as shown below:

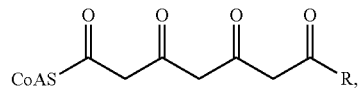

wherein "CoA" is coenzyme A and "R" is an alkyl group. For example, when hexanoic acid is used as the starting feed for cannabinoid production, the hexanoyl-CoA formed by the acyl-CoA synthetase, e.g., revS or CsAA3, as described above is condensed with three molecules of malonyl-CoA to form 3,5,7-trioxododecanoyl-CoA (i.e., "R" is an n-pentyl group). Type III PKSs are homodimeric enzymes that act directly on acyl-CoA substrates (as opposed to acyl carrier protein-bound substrates, in the case of type I PKSs and type II PKSs). Type III PKSs are well characterized, for example, by Yu et al. (*IUBMB Life,* 64(4): 285-295, 2012).

In some embodiments, an olivetolic acid synthase polynucleotide encodes a polypeptide that comprises an amino acid sequence that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:4. In some embodiments, the olivetolic acid synthase polynucleotide encodes a type III PKS comprising an amino acid sequence that has about 70%, 75%, 80%, 85%, 90%, 95%, or greater identity to the sequence set forth in SEQ ID NO:4.

2-Alkyl-4,6-dihydroxybenzoic Acid Cyclase

A host cell in accordance with the invention may be further modified to express an exogenous polynucleotide that encodes a 2-alkyl-4,6-dihydroxybenzoic acid cyclase (e.g., olivetolic acid cyclase). In some embodiments, the 2-alkyl-4,6-dihydroxybenzoic acid cyclase is a dimeric α+β barrel (DABB) protein domain that resembles DABB-type polyketide cyclases from *Streptomyces*. Olivetolic acid cyclase is described, for example, by Gagne et al. (*Proc. Nat. Acad. Sci. USA* 109 (31): 12811-12816; 2012). The term "2-alkyl-4,6-dihydroxybenzoic acid cyclase" includes variants, e.g., a truncated or modified polypeptide, that have cyclase activity; and naturally occurring homologs or orthologs. In some embodiments, the 2-alkyl-4,6-dihydroxybenzoic acid cyclase is olivetolic acid synthase from *C. sativa* (EC number 4.4.1.26). In some embodiments, the 2-alkyl-4,6-dihydroxybenzoic acid cyclase is a divarinic acid cyclase (see, e.g., Yang et al., *FEBS J.* 283:1088-1106, 2016). In some embodiments, the 2-alkyl-4,6-dihydroxybenzoic acid cyclase is an olivetolic acid cyclase homolog from *Arabidopsis thaliana* AtHS1 (Uniprot Q9LUV2), *Populus tremula* SP1 (P0A881), *A. thaliana* At5g22580 (Q9FK81), *S. glaucescens* TcmI cyclase (P39890), *S. coelicolor* ActVA-Orf6 (Q53908), *P. reinekei* MLMI (C5MR76), *S. nogalater* SnoaB (O54259), *M. tuberculosis* Rv0793 (O86332), or *P. aeruginosa* PA3566 (Q9HY51). In some embodiments, the 2-alkyl group of the 2-alkyl-4,6-dihydroxybenzoic acid contains 1-18 carbon atoms. In some embodiments, the 2-alkyl group of the 2-alkyl-4,6-dihydroxybenzoic acid contains 1-12 carbon atoms. In some embodiments, the 2-alkyl group of the 2-alkyl-4,6-dihydroxybenzoic acid contains 1-9 carbon atoms.

In some embodiments, the polynucleotide encoding the 2-alkyl-4,6-dihydroxybenzoic acid cyclase encodes a polypeptide that has about 60% or greater identity (e.g., about 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity) to the sequence set forth in SEQ ID NO:5, 6, or 7. In some embodiments, the polypeptide has about 70%, 75%, 80%, 85%, 90%, 95%, or greater identity to the sequence set forth in SEQ ID NO:5, 6, or 7.

In some embodiments, a modified recombinant host cell engineered to express an acyl-CoA synthetase, an olivetolic acid synthase, and a 2-alkyl-4,6-dihydroxybenzoic acid cyclase (e.g., olivetolic acid cyclase), may be further modified to express an exogenous polynucleotide that encodes a prenyltransferase that catalyzes coupling of geranyl-pyrophosphate to a 2-alkyl-4,6-dihydroxybenzoic acid (e.g., olivetolic acid) to produce acidic cannabinoids such as cannabigerolic acid (CBGA). Examples of prenyltransferases include geranylpyrophosphate:olivetolate geranyltransferase (GOT; EC 2.5.1.102) as described by Fellermeier & Zenk (*FEBS Letters* 427:283-285; 1998). *Streptomyces* prenyltransferases including NphB, as described by Kumano et al. (*Bioorg Med Chem.* 16(17): 8117-8126; 2008), can also be used in accordance with the invention. In some embodiments, the prenyltransferase is fnq26: Flaviolin linalyltransferase from *Streptomyces cinnamonensis*. In some embodiments, a host cell genetically modified to express the prenyltransferase may be a modified host cell as described in the following section.

Thus, as detailed herein, in some embodiments relating to the biosynthesis of an initiating aromatic polyketide precursor, enzymes that form simple starting units are expressed and used to generate, from exogenously supplied aliphatic carboxylic acids, acylthioesters, typically acetyl-, propionyl-, butanoyl-, hexanoyl-, malonyl- or methylmalonyl-coenzyme-A (CoA) thioesters. These are then condensed repeatedly with malonyl-CoA to form the aromatic polyketide building blocks for the next step in cannabinoid biosynthesis, namely prenylation.

In some embodiments, the starting carboxylic acids are butanoic acid and hexanoic acid, giving rise to precursors for the eventual production of cannabigerovarinic acid- and cannabigerolic acid-type molecules respectively and then their decarboxylated, and otherwise chemically transformed, derivatives.

In still other embodiments, the present invention provides methods for contacting engineered host cells with media containing high levels of prenol, isoprenol or geraniol either in batch processes or in fed-batch processes, wherein olivetolic acid or an olivetolic acid analog is also contacted with the host cells, or is biosynthesized within the engineered yeast cells through the actions of a hexanoyl-CoA synthetase, a type III PKS and a cyclase enzyme as described above.

Also provided herein are modified recombinant host cells comprising: (i) a first exogenous polynucleotide that encodes prenol and isoprenol kinase; (ii) a second exogenous polynucleotide that encodes kinase activity to produce dimethylallyl pyrophosphate and isopentenyl pyrophosphate when grown in the presence of exogenous prenol and isoprenol; (iii) a third exogenous polynucleotide that encodes a geranyl-pyrophosphate synthase; and (iv) a fourth exogenous polynucleotide that encodes a prenyltransferase that catalyzes coupling of geranyl-pyrophosphate to olivetolic acid or an olivetolic acid analog (e.g., a 2-alkyl-4,6-dihydroxybenzoic acid) to form a cannabinoid compound. In some embodiments, the 2-alkyl group of the 2-alkyl-4,6-dihydroxybenzoic acid contains 1-18 carbon atoms. In some embodiments, the 2-alkyl group of the 2-alkyl-4,6-dihydroxybenzoic acid contains 1-12 carbon atoms. In some embodiments, the 2-alkyl group of the 2-alkyl-4,6-dihydroxybenzoic acid contains 1-9 carbon atoms.

5-Carbon prenols (prenol and isoprenol) may be converted by several enzymes to the monophosphate level and then to the diphosphate level by additional expressed enzymes, prior to their coupling to give the 10-carbon geranyl-diphosphate by the enzyme GPP-synthase. In some embodiments, the initial kinase event is performed by the enzyme hydroxyethylthiazole kinase. This enzyme has been described in several organisms from where the encoding genes are derived, including *E. coli, Bacillus subtilis, Rhizobium leguminosarum, Pyrococcus horikoshii, S. cerevisiae* and maize species.

Further phosphorylation to the diphosphate level is achieved by using the enzyme isoprenyl diphosphate synthase or isopentenylphosphate kinase, see U.S. Pat. No. 6,235,514. In some embodiments, chemically synthesized genes encoding this enzyme or more active mutants are derived by using the *Thermoplasma acidophilum, Methanothermobacter thermautotrophicus, Methano-caldococcus jannaschii, Mentha* x *piperita* or *Mangifera indica* amino acid sequences, or other homologous sequences with kinase activity.

The 10-carbon geranyl-diphosphate may also be generated by a kinase that phosphorylates geraniol to the monophosphate level, followed by a second kinase that gives rise to geranyl-diphosphate. In some embodiments, the first kinase event is performed by the enzyme farnesol kinase (FOLK) (Fitzpatrick, Bhandari and Crowell, 2011; Plant J. 2011 June; 66(6):1078-88). This kinase enzyme is derived from the known amino acid sequences or mutants from the organisms that phosphorylate the 5-carbon prenols, including plants (*Arabidopsis thaliana, Camelina sativa, Capsella rubella, Noccaea caerulescens* etc.) and fungi (*Candida albicans, Talaromyces atroroseus*, etc.).

Further phosphorylation of geranyl-phosphate to the geranyl-diphosphate level is achieved by using a mutated enzyme isopentenyl monophosphate kinase (IPK) Mutations in IPK (Val73, Val130, Ile140) have been reported to give rise to enhanced geranyl-phosphate kinase activity (Mabanglo et al., 2012). This kinase enzyme is derived from the known amino acid sequences or mutants from bacteria or archaeal species, including but not limited to *Methanocaldococcus jannaschii*, and *Thermoplasma acidophilum.*

In some embodiments, the DNA construct for the prenylase geranyl diphosphate:olivetolate geranyltransferase encodes the wild type or a mutant enzyme with yeast-preferred codons. In others, DNA constructs that encode bacterial, e.g., *Streptomyces* prenyltransferases with relaxed substrate specificities are used (Kumano et al., 2008).

In some embodiments, the host cell comprises one or more additional exogenous polynucleotides selected from the three following exogenous polynucleotides: an exogenous polynucleotide that encodes a prenol and isoprenol kinase; an exogenous polynucleotide that encodes a kinase that produces dimethylallyl pyrophosphate and isopentenyl pyrophosphate when grown in the presence of exogenous prenol and isoprenol; and an exogenous polynucleotide that encodes a geranyl-pyrophosphate synthase.

In contrast to previously described methodologies for the recombinant DNA-based production of cannabinoids in yeast, some embodiments of the present invention are based on the high aqueous solubility of both prenol and isoprenol together with the ability to generate recombinant host cells that express at high levels, heterologous kinase enzymes that can phosphorylate these 5-carbon compounds to the diphosphate level, thereby trapping them, due to the charged diphosphate moieties, within the host cell.

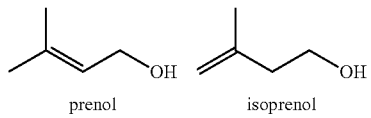

In some embodiments, the resulting diphosphates are then condensed to form geranyl-diphosphate (or pyrophosphate) through the action of either endogenous or heterologously expressed geranyl-pyrophosphate synthase (GPP synthase) according to the schematic shown in FIG. 1. This is then available for condensation with a 2-alkyl-4,6-dihydroxybenzoic acid through the action of a wild type or preferably a more active mutant aromatic prenyltransferase enzyme to form cannabigerolic acid or a cannabigerolic acid analog.

In other embodiments, geraniol itself is converted, through the actions of heterologously expressed kinase enzymes to form geranyl-pyrophosphate, which is then coupled with olivetolic acid or an olivetolic acid analog (e.g., 2-alkyl-4,6-dihydroxybenzoic acid), through the action of a wild-type prenyltransferase or a mutant prenyltransferase enzyme, to form cannabigerolic acid or a cannabigerolic acid analog.

In some embodiments, host cells are further modified to express a CBDA synthase (EC 1.21.3.8), a THCA synthase, or CBCA synthase as further described below.

Engineering the Host Cell

Polynucleotide can be introduced into host cells using any methodology. In some embodiments, exogenous polynucleotides encoding two or more enzymes, e.g., two of acyl-CoA synthetase, olivetolic acid synthase, such as revS or CsAAE3, and a 2-alkyl-4,6-dihydroxybenzoic acid cyclase (e.g., olivetolic) acid cyclase as described herein are present in the same expression construct, e.g., an autonomously replicating expression vector, and expressed as a multicistronic RNA in which expression is driven by the same promoter. Thus, for example, in some embodiments, an exogenous polynucleotide encoding olivetolic acid synthase and an exogenous polynucleotide encoding 2-alkyl-4,6-dihydroxybenzoic acid cyclase (e.g., olivetolic acid cyclase), are contained in the same expression construct, e.g., and autonomously replicating expression vector, and separated by an internal ribosome entry site (IRES) such expression is drive by the same promoter to generate a discistronic mRNA. In some embodiments, the promoter is an alcohol dehydrogenase-2 promote. In some embodiments, exogenous polynucleotides are present in the same expression construct, e.g., an autonomously replicating expression vector, and are operably linked to separate promoters. In some embodiments, exogenous polynucleotides are present in two or more expression constructs, e.g., autonomously replicating expression vectors. In some embodiments, the autonomously replicating expression vector is a yeast artificial chromosome. In some embodiments, one or more of the exogenous polynucleotides are integrated into the host genome. In some embodiments, multiple exogenous polynucleotides are introduced into the host cell by retrotransposon integration.

In some embodiments, a cannabinoid compound is produced using olivetolic acid or olivetolic acid analog that is expressed within the host cell, e.g., as described in the preceding paragraph, and the host cell is further modified to express a prenyltransferase, prenol and isoprenol kinase; a kinase to produce dimethylallyl pyrophosphate and isopentenyl pyrophosphate when grown in the presence of exogenous prenol and isoprenol; or a polynucleotide that encodes a geranyl-pyrophosphate synthase as described herein. Such polynucleotides may be contained in the same or separate expression vectors as described in the preceding paragraph.

In some embodiments, the modified recombinant host cell further comprises an exogenous polynucleotide that encodes a cannabinoid synthase enzyme that catalyzes conversion of a first cannabinoid compound intermediate produced in the host cell to form a second cannabinoid compound.

Host Cells

In some embodiments, the host cell is a yeast or a filamentous fungus host cell such as an *Aspergillus* host cell. Genera of yeast that can be employed as host cells include, but are not limited to, cells of *Saccharomyces, Schizosaccharomyces, Candida, Hansenula, Pichia, Kluyveromyces, Yarrowia* and *Phaffia*. Suitable yeast species include, but are not limited to, *Saccharomyces cerevisiae, Schizosaccharomyces pombe, Candida albicans, Hansenula polymorpha, Pichia pastoris, P. canadensis, Kluyveromyces marxianus, Kluyveromyces lactis, Phaffia rhodozyma* and, *Yarrowia lipolytica*. Filamentous fungal genera that can be employed as host cells include, but are not limited to, cells of *Acremonium, Aspergillus, Aureobasidium, Bjerkandera, Ceriporiopsis, Chrysoporium, Coprinus, Coriolus, Corynascus, Chaertomium, Cryptococcus, Filobasidium, Fusarium, Gibberella, Humicola, Magnaporthe, Mucor, Myceliophthora, Mucor, Neocallimastix, Neurospora, Paecilomyces, Penicillium, Phanerochaete, Phlebia, Piromyces, Pleurotus, Scytaldium, Schizophyllum, Sporotrichum, Talaromyces, Thermoascus, Thielavia, Tolypocladium, Trametes*, and *Trichoderma*. Illustrative species of filamentous fungal species include *Aspergillus awamori, Aspergillus fumigatus, Aspergillus foetidus, Aspergillus japonicus, Aspergillus nidulans, Aspergillus niger, Aspergillus oryzae, Chrysosporium lucknowense, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium soliturn, Penicillium funiculosum Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum, Trichoderma reesei*, and *Trichoderma viride*.

In some embodiments, the host cell is selected from the group consisting of *Saccharomyces cerevisiae, Kluyveromyces lactis, Kluyveromyces marxianus, Pichia pastoris, Yarrowia lipolytica, Hansenula polymorpha* and *Aspergillus*.

In the above embodiments, the genes may be encoded by chemically synthesized genes, with yeast codon optimization, that encode a wild type or mutant enzyme from *C. sativa, Arabidopsis thaliana* or *Pseudomonas* spp.

Promoters used for driving transcription of genes in *S. cerevisiae* and other yeasts are well known in the art and include DNA elements that are regulated by glucose concentration in the growth media, such as the alcohol dehydrogenase-2 (ADH2) promoter. Other regulated promoters or inducible promoters, such as those that drive expression of the GAL1, MET25 and CUP1 genes, are used when conditional expression is required. GAL1 and CUP1 are induced by galactose and copper, respectively, whereas MET25 is induced by the absence of methionine.

In some embodiments, one or more of the exogenous polynucleotides is operably linked to a glucose regulated promoter. In some embodiments, expression of one or more of the exogenous polynucleotides is driven by an alcohol dehydrogenase-2 promoter.

Other promoters drive strongly transcription in a constitutive manner. Such promoters include, without limitation, the control elements for highly expressed yeast glycolytic enzymes, such as glyceraldehyde-3-phosphate dehydrogenase (GPD), phosphoglycerate kinase (PGK), pyruvate kinase (PYK), triose phosphate isomerase (TPI) and alcohol dehydrogenase-1 (ADH1). Another strong constitutive promoter that may be used is that from the *S. cerevisiae* transcription elongation factor EF-1 alpha gene (TEF1) (Partow et al., Yeast. 2010, (11):955-64).

In other embodiments, the host cells can increase cannabinoid production by increasing precursor pools and the like. Heterologous natural or chemically synthesized genes for enzymes such as malonyl-CoA synthase, acetyl-CoA carboxylase, acetyl-CoA synthases-1 and -2, gene products in the mevalonate pathway, e.g., HMG-CoA reductase, mevalonate kinase, mutant farnesyl-pyrophosphate synthase (ERG20; Zhao et al., 2016) from *Saccharomyces* or other eukaryotic species may be introduced on high-level expression plasmid vectors or through genomic integration using methods well known to those skilled in the art. Such methods may involve CRISPR Cas-9 technology, yeast artificial chromosomes (YACs) or the use of retrotransposons. Alternatively, if natural to the host organism, such genes may be up-regulated by genetic element integration methods known to those skilled in the art.

In yet other aspects, similar engineering may be employed to reduce the production of natural products, e.g., ethanol that utilize carbon sources that lead to reduced utilization of that carbon source for cannabinoid production. Such genes may be completely "knocked out" of the genome by deletion, or may be reduced in activity through reduction of promoter strength or the like. Such genes include those for the enzymes ADH1 and/or ADH6. Other gene "knockouts" include genes involved in the ergosterol pathway, such as ERG9 and the two most prominent aromatic decarboxylase genes of yeast, PAD1 and FDC1.

Further embodiments include genes for accessory enzymes aimed at assisting in the production of the final product cannabinoids. One such enzyme, catalase, is able to neutralize hydrogen peroxide produced by certain enzymes involved in the oxido-cyclization of CBGA and analogs, such as cannabidiolic acid synthase (Taura et al., 2007), $\Delta^9$-tetrahydrocannabinolic acid synthase (Sirikantaramas et al., 2004) and cannabichromenic acid synthase (Morimoto et al., 1998).

In further embodiments, the engineered host cells contain up-regulated or down-regulated endogenous or heterologous genes to optimize, for example, the precursor pools for cannabinoid biosynthesis. Additional, further heterologous gene products may be expressed to give "accessory" functions within the cell. For example, overexpressed catalase may be expressed in order to neutralize hydrogen peroxide formed in the oxido-cyclization step to important acidic cannabinoids such as CBDA, $\Delta^9$-THCA and CBCA. "Accessory" genes and their expressed products may be provided through integration into the yeast genome through techniques well known in the art, or may be expressed from plasmids (also known as yeast expression vectors), yeast artificial chromosomes (YACs) or yeast transposons.

In some embodiments, host cells, e.g., yeast strains, transformed or genomically integrated with plasmids or vectors containing each of the above genes are transformed together with another expression system for the conversion of CBGA or a CBGA analog to a second acidic cannabinoid, as further explained below. In some such embodiments, the expression system is on the same vector or on a separate vector, or is integrated into the host cell genome.

The cannabinoid-producing engineered cells of the invention may be made by transforming a host cell, either through genomic integration or using episomal plasmids (also referred to as expression vectors, or simply vectors) with at least one nucleotide sequence encoding enzymes involved in the engineered metabolic pathways. As used herein the term "nucleotide sequence", "nucleic acid sequence" and "genetic construct" are used interchangeably and mean a polymer of RNA or DNA, single- or double-stranded, optionally containing synthetic, non-natural or altered nucleotide bases. A nucleotide sequence may comprise one or more segments of cDNA, genomic DNA, synthetic DNA, or RNA. In some embodiments, the nucleotide sequence is codon-optimized to reflect the typical codon usage of the host cell without altering the polypeptide encoded by the nucleotide sequence. In certain embodiments, the term "codon optimization" or "codon-optimized" refers to modifying the codon content of a nucleic acid sequence without modifying the sequence of the polypeptide encoded by the nucleic acid to enhance expression in a particular host cell. In certain embodiments, the term is meant to encompass modifying the codon content of a nucleic acid sequence as a means to control the level of expression of a polypeptide (e.g., either increase or decrease the level of expression). Accordingly, described are nucleic sequences encoding the enzymes involved in the engineered metabolic pathways. In some embodiments, a metabolically engineered cell may express one or more polypeptide having an enzymatic activity necessary to perform the steps described below. In some embodiments, the nucleotide sequences are synthesized and codon-optimized for expression in yeast according to methods described in U.S. Pat. No. 7,561,972.

For example a particular cell may comprises one, two, three, four, five or more than five nucleic acid sequences, each one encoding the polypeptide(s) necessary to produce a cannabinoid compound, or cannabinoid compound intermediate described herein. Alternatively, a single nucleic acid molecule can encode one, or more than one, polypeptide. For example, a single nucleic acid molecule can contain nucleic acid sequences that encode two, three, four or even five different polypeptides. Nucleic acid sequences useful for the invention described herein may be obtained from a variety of sources such as, for example, amplification of cDNA sequences, DNA libraries, de novo synthesis, excision of genomic segment. The sequences obtained from such sources may then be modified using standard molecular biology and/or recombinant DNA technology to produce nucleic sequences having desired modifications. Exemplary methods for modification of nucleic acid sequences include, for example, site directed mutagenesis, PCR mutagenesis, deletion, insertion, substitution, swapping portions of the sequence using restriction enzymes, optionally in combination with ligation, homologous recombination, site specific recombination or various combination thereof. In other embodiments, the nucleic acid sequences may be a synthetic nucleic acid sequence. Synthetic polynucleotide sequences may be produced using a variety of methods described in U.S. Pat. No. 7,323,320, as well as U.S. Pat. Appl. Pub. Nos. 2006/0160138 and 2007/0269870. Methods of transformation of yeast cells are well known in the art.

IV. Methods for Cannabinoid Expression

Fermentation Conditions

Cannabinoid production according to the methods provided herein generally includes the culturing of host cells (e.g., yeast or filamentous fungi) that have been engineered to contain the expression systems described above. In some embodiments, the carbon sources for yeast growth are sugars such as glucose, dextrose, xylose, or other sustainable feedstock sugars such as those derived from cellulosic sources, for example. In other embodiments, the carbon sources used may be methanol, glycerol, ethanol or acetate. In some embodiments, feedstock compositions are refined by experimentation to provide for optimal yeast growth and final cannabinoid production levels, as measured using analytical techniques such as HPLC. In such embodiments, methods include utilization of glucose/ethanol or glucose/acetate mixtures wherein the molar ratio of glucose to the 2-carbon source (ethanol or acetate) is between the ranges of 50/50, 60/40, 80/20, or 90/10. Feeding is optimized to both induce glucose-regulated promoters and to maximize the production of acetyl-CoA and malonyl-CoA precursors in the production strain.

In additional aspects of the invention, olivetolic acid or its analogs may be obtained by chemical synthesis, or may be biosynthesized in recombinant production systems. In some embodiments, olivetolic acid is produced at high levels in the same yeast cell strain as contains the metabolic pathways for cannabinoid production. High-level production systems for monocyclic polyketide aromatics in yeast are known in the field, see U.S. Pat. No. 9,637,763. In other embodiments, media from yeast strains that are producing high levels of olivetolic acid or its analogs can be concentrated and used as a highly compatible feedstock in the MPF procedure for cannabinoid manufacture.

Fermentation methods may be adapted to a particular yeast strain due to differences in their carbon utilization pathway or mode of expression control. For example, a *Saccharomyces* yeast fermentation may require a single glucose feed, complex nitrogen source (e.g., casein hydrolysates), and multiple vitamin supplementation. This is in contrast to the methylotrophic yeast *Pichiapastoris* which may require glycerol, methanol, and trace mineral feeds, but only simple ammonium (nitrogen) salts, for optimal growth and expression. See, e.g., Elliott et al. J. Protein Chem. (1990) 9:95 104, U.S. Pat. No. 5,324,639 and Fieschko et al. Biotechnol. Bioeng. (1987) 29:1113 1121. Culture media may contain components such as yeast extract, peptone, and the like. The microorganisms can be cultured in conventional fermentation modes, which include, but are not limited to, batch, fed-batch, and continuous flow.

In some embodiments, the rate of glucose addition to the fermenter is controlled such that the rate of glucose addition is approximately equal to the rate of glucose consumption by the yeast; under such conditions, the amount of glucose or ethanol does not accumulate appreciably. The rate of glucose addition in such instances can depend on factors including, but not limited to, the particular yeast strain, the fermentation temperature, and the physical dimensions of the fermentation apparatus.

For the MPF procedure, in batch mode, the precursors olivetolic acid (or an olivetolic acid analog such as another 2-alkyl-4,6-dihydroxybenzoic acid), prenol, isoprenol or geraniol may be present in concentrations of between 0.1 and 50 grams/L (e.g., between 1 and 10 g/L). In fed-batch mode, the precursors may be fed slowly into the fermentation over between 2 and 20 hours, such that a final addition of between 1 and 100 grams/L (e.g., between 1 and 10 grams/L, or between 10 and 100 grams/L) of each requisite precursor occurs.

Similarly, carboxylic acid starting materials such as hexanoic acid, butanoic acid, pentanoic acid, and the like may be present in concentrations of between 0.1 and 50 grams/L (e.g., between 1 and 10 g/L). In fed-batch mode, the carboxylic acid may be fed slowly into the fermentation over between 2 and 20 hours, such that a final addition of between 1 and 100 grams/L (e.g., between 1 and 10 grams/L, or between 10 and 100 grams/L) of the carboxylic acid occurs.

Culture conditions such as expression time, temperature, and pH can be controlled so as to afford target cannabinoid intermediates (e.g., olivetolic acid) and/or target cannabinoid products (e.g., CBGA, CBG) in high yield. Host cells are generally cultured in the presence of starting materials, such as hexanoic acid, prenol, isoprenol, or the like, for periods of time ranging from a few hours to a day or longer (e.g., 24 hours, 30 hours, 36 hours, or 48 hours) at temperatures ranging from about 20° C. to about 40° C. depending on the particular host cells employed. For example, *S. cerevisiae* may be cultured at 25-32° C. for 24-40 hours (e.g., 30 hours). The pH of culture medium can be maintained at a particular level via the addition of acids, bases, and/or buffering agents. In certain embodiments, culturing yeast at a pH of 6 or higher can reduce the production of unwanted side products such as olivetol. In some embodiments, the pH of the yeast culture ranges from about 6 to about 8. In some embodiments, the pH of the yeast culture is about 6.5. In some embodiments, the pH of the yeast culture is about 7. In some embodiments, the pH of the yeast culture is about 8.

In some embodiments, a recombinant yeast cell is genetically modified such that it produces, when cultured in vivo in a suitable precursor-containing media as described above, the cannabinoid product of interest or an intermediate at a level of at least about 0.1 g/L, at least about 0.5 g/L, at least about 0.75 g/L, at least about 1 g/L, at least about 1.5 g/L, at least about 2 g/L, at least about 2.5 g/L, at least about 3 g/L, at least about 3.5 g/L, at least about 4 g/L, at least about 4.5 g/L, at least about 5 g/L, at least about 5.5 g/L, at least about 6 g/L, at least about 7 g/L, at least about 8 g/L, at least about 9 g/L, or at least 10 g/L. In some embodiments, a recombinant yeast cell is genetically modified such that it produces, when cultured in vivo in a suitable medium, the cannabinoid product of interest or an intermediate at a level of at least about 20 g/L, at least about 30 g/L, at least about 50 g/L, or at least about 80 g/L.

Cannabinoid production may be carried out in any vessel that permits cell growth and/or incubation. For example, a reaction mixture may be a bioreactor, a cell culture flask or plate, a multiwell plate (e.g., a 96, 384, 1056 well microtiter plates, etc.), a culture flask, a fermenter, or other vessel for cell growth or incubation. Biologically produced products of interest may be isolated from the fermentation medium or cell extract using methods known in the art. For example, solids or cell debris may be removed by centrifugation or filtration. Products of interest may be isolated, for example, by distillation, liquid-liquid extraction, membrane evaporation, adsorption, or other methods.

Conversion of 2-Alkyl-4,6-Dihydroxybenzoic Acids Acid to Cannabinoid Products

Also provided herein are methods for producing cannabinoid products. In some embodiments, the methods include expressing a cannabinoid starting material in a yeast cell, wherein the yeast cell is genetically modified to express the cannabinoid starting material, isolating the yeast cell, and converting the cannabinoid starting material to the cannabinoid product in the isolated yeast cell. The cannabinoid starting material can be an acidic cannabinoid, a neutral cannabinoid, or a cannabinoid precursor such as olivetolic acid or another 2-alkyl-4,6-dihydroxybenzoic acid. Converting the cannabinoid starting material can be conducted using the procedures described herein (e.g., chemical or enzymatic geranylation, thermal or enzymatic decarboxylation, etc.) or can be modified according to the identity of the particular cannabinoid starting material or the particular cannabinoid product. The cannabinoid starting material can be expressed, for example, using any of the expression systems described above. Isolating the yeast cells can optionally include: collecting yeast cells from culture media by centrifugation, filtration, or other means; washing yeast cells to remove culture media or other components; removing at least a portion of liquid (e.g., culture media) from the cells; and/or drying the cells (e.g., by lyophilization or other means). Isolated yeast cells can be directly subjected to reaction conditions for forming the cannabinoid products. For example, yeast cells can be combined directly with solvents and other reagents as described below.

In some embodiments, the methods include culturing modified recombinant host cells containing an expression system as described above under conditions in which a 2-alkyl-4,6-dihydroxybenzoic acid is produced, and converting the 2-alkyl-4,6-dihydroxybenzoic acid to the cannabinoid product. In some embodiments, the methods include culturing modified recombinant host cells containing an expression system as described above under conditions in which olivetolic acid is produced, and converting the olivetolic acid to the cannabinoid product.

In some embodiments, the converting step is conducted in vitro. For example, the converting step can include forming a reaction mixture comprising a 2-alkyl-4,6-dihydroxybenzoic acid (e.g., olivetolic acid), geraniol, and an organic solvent under conditions sufficient to produce an acidic cannabinoid (e.g., cannabigerolic acid, CBGA). The method can be employed to convert olivetolic acid analogs to the corresponding acidic cannabinoids.

Any suitable organic solvent can be used in the methods of the invention. Suitable solvents include, but are not limited to, toluene, methylene chloride, ethyl acetate, acetonitrile, tetrahydrofuran, benzene, ethylbenzene, xylenes (i.e., m-xylene, o-xylene, p-xylene, or any combination thereof), chloroform, diethyl ether, dimethyl formamide, dimethyl sulfoxide, petroleum ether, and mixtures thereof. In some embodiments, the organic solvent is toluene, benzene, ethylbenzene, xylenes, or a mixture thereof. In some embodiments, the organic solvent is toluene. Aqueous organic solvent mixtures (i.e., a mixture of water and a water-miscible organic solvent such as tetrahydrofuran or dimethyl formamide) can also be employed. In general, the ratio of the solvent to the 2-alkyl-4,6-dihydroxybenzoic acid ranges from about 1:1 to about 1000:1 by weight. The ratio of the solvent to 2-alkyl-4,6-dihydroxybenzoic acid can be, for example, about 100:1 by weight, or about 10:1 by weight, or about 5:1 weight. In certain embodiments, the 2-alkyl-4,6-dihydroxybenzoic acid is present in a yeast mixture (e.g., dried yeast cells, or a wet yeast cell pellet collected from culture). In some such embodiments, the reaction mixture comprises the host cell (e.g., dried yeast cells). The ratio of solvent to yeast mixture (e.g., dried yeast cells) can range from about 1:1 to about 1000:1 by weight. The ratio of the solvent to the yeast mixture can be, for example, about 100:1 by weight, or about 10:1 by weight, or about 5:1 by weight, or about 2:1 by weight.

Any suitable amount of geraniol can be used in the conversion step. In general, the reaction mixture contains at least one molar equivalent of geraniol with respect to the 2-alkyl-4,6-dihydroxybenzoic acid. The reaction mixture can contain, for example, from about 1 molar equivalent to about 10 molar equivalents of geraniol with respect to the 2-alkyl-4,6-dihydroxybenzoic acid (e.g., about 1.1 molar equivalents, or about 1.2 molar equivalents, or about 2 molar equivalents). Geraniol derivatives (e.g., geranyl bromide, geranyl chloride, geranyl tosylate, geranyl mesylate, and the like) can also be employed in the conversion step).

In some embodiments, the reaction mixture further comprises an acid. Any suitable acid can be used in the conversion step. Examples of suitable acids include, but are not limited to, hydrochloric acid, sulfuric acid, nitric acid, formic acid, acetic acid, trifluoroacetic acid, p-toluenesulfonic acid, methanesulfonic acid, and trifluoromethane sulfonic acid. In some embodiments, the acid is a sulfonic acid. In some embodiments, the acid is p-toluenesulfonic acid. Any suitable amount of the acid can be used in the conversion step. In general, the reaction mixture contains from about 0.01 molar equivalents of the acid (e.g., p-toluenesulfonic acid) to about 10 molar equivalents of the acid with respect to the 2-alkyl-4,6-dihydroxybenzoic acid. The reaction mixture can contain, for example, from about 1 molar equivalent to about 10 molar equivalents of geraniol with respect to the 2-alkyl-4,6-dihydroxybenzoic acid (e.g., about 0.01 molar equivalents, or about 0.1 molar equivalents).

The converting step can be conducted at any suitable temperature. Typically, the conversion step is conducted at temperatures ranging from about 20° C. to about 200° C., e.g., from about 25° C. to about 100° C., or from about 25° C. to about 80° C., or from about 25° C. to about 70° C. The conversion step is conducted for a period of time sufficient to convert the 2-alkyl-4,6-dihydroxybenzoic acid to the cannabinoid product (e.g., to convert olivetolic acid to CBGA). Depending on factors such as the particular acid employed, the particular solvent employed, and the state of the 2-alkyl-4,6-dihydroxybenzoic acid (e.g., present in a yeast mixture), the conversion time will range from a few minutes to several hours. In some embodiments, the reaction mixture will be maintained at a temperature ranging from about 25° C. to about 100° C. (e.g., about 60° C.) for a period of time ranging from about 5 minutes to about 360 minutes. In some embodiments, the reaction mixture is maintained at or around 60° C. for 60 minutes or less (e.g., about 55 minutes, or about 30 minutes, or about 15 minutes, or about 10 minutes).

In some embodiments, an acidic cannabinoid such as CBGA is the cannabinoid product. In some embodiments, the method further includes converting the acidic cannabinoid, e.g., CBGA, to the cannabinoid product. The final cannabinoid product can be a neutral cannabinoid or another acidic cannabinoid. In some embodiments, conversion of an intermediate compound such as CBGA to another cannabinoid is carried out via physical or chemical processes such as heating, auto-oxidation or UV light treatment. For example, the methods can include the decarboxylation of acidic cannabinoid, either within the engineered yeast cells or following their full or partial purification through the action of heat or through the action of a wild-type or mutant decarboxylase enzyme contacting the cannabinoid acid in vivo or in vitro. Decarboxylation of the acidic cannabinoids provides corresponding neutral cannabinoids; decarboxylation of CBGA, for example, provides CBG.

In some embodiments, UV light treatment, heating, oxidation, or other reaction conditions are employed such that a first intermediate recombinant DNA-derived cannabinoid product is retained within the yeast cells and is then converted to a second valuable cannabinoid product that is isolated and purified at commercial scale.

Additional chemical transformations may be performed on the cannabinoids formed to make fully non-natural analogs such as esters, ethers and halogenated derivatives, either for use as pro-drugs, or more active or bioavailable drug substances. In some embodiments, this chemistry may be performed on whole yeast cells that harbor the biosynthetic cannabinoid substrates in order to avoid unnecessary purification steps prior to formation of the desired final product.

In still other embodiments, described is a method for conversion of a first intermediate cannabinoid to a second cannabinoid through the action of a wild type or a mutant cannabinoid or cannabinoid acid synthase, either within the same engineered host cell or through co-culturing with two or more recombinant host cell strains, e.g., yeast strains.

As explained above, in some embodiments, host cells, e.g., yeast strains, transformed or genomically integrated with plasmids or vectors containing each of the above genes are transformed together with another expression system for the conversion of CBGA or a CBGA analog to a second acidic cannabinoid. In some such embodiments, the expression system is on the same vector or on a separate vector, or is integrated into the host cell genome. In other embodiments, the expression system for the conversion activity encodes one of the *C. sativa* enzymes THCA synthase, CBDA synthase or CBCA synthase. In some embodiments, the synthase is a homolog from hops, e.g., a CBDA synthase homolog from hops.

In some embodiments, an acidic cannabinoid, e.g., CBGA or CBDA, may be decarboxylated to form a neutral cannabinoid compound, e.g., CBG or CBD, using a decarboxylase, e.g., *Aspergillus nidulans* orsB decarboxylase. Alternatively, an acidic cannabinoid can be decarboxylated by maintaining the acidic cannabinoid at an elevated temperature (e.g., around 40° C., 50° C., or 100° C.) for periods of time ranging from a few minutes to several hours.

The invention illustratively described herein suitably may be practiced in the absence of any element or elements, limitation or limitations that are not specifically disclosed herein. Thus, for example, in each instance herein any of the terms "comprising", "consisting essentially of" and "consisting of" may be replaced with either of the other two terms. Thus, for example, some embodiments may encompass a host cell "comprising" a number of components, other embodiments would encompass a host cell "consisting essentially of" the same components, and still other embodiments would encompass a host cell "consisting of" the same components. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art. All patents, patent applications, and literature references cited in the present specification are hereby incorporated by reference in their entirety.

V. Examples

The following examples are offered to illustrate, but not to limit the claimed invention.

Example 1—MPF-Based Expression of CBGA in Saccharomyces cerevisiae

The *S. cerevisiae* ADH2 promoter is chemically synthesized and fused to a synthetic gene for a mutated bacterial NphB gene from *Streptomyces coelicolor*. The gene is linked to a synthetic gene for *S. cerevisiae* ERG20 with a synthetic sequence for the *S. cerevisiae* p150 internal ribosome entry site (IRES) sequence. A *S. cerevisiae* terminator sequence is also fused to the gene sequence, immediately subsequent to the stop codon(s) of the ERG20 gene. The expression cassette is cloned into a yeast expression vector containing the URA3 selectable marker. Similarly, a gene encoding the *S. cerevisiae* hydroxyethylthiazole kinase enzyme and a *Thermoplasma acidophilum* isopentenyl-phosphate kinase mutant (V73I+Y141V+K203G) gene, also linked by the *S. cerevisiae* p150 internal ribosome entry site (IRES), is cloned into a yeast expression vector containing the selectable marker for growth in tryptophan-deficient media. A *S. cerevisiae* terminator sequence is also fused to this dicistronic sequence, immediately subsequent to the stop codon(s) of the *T. acidophilum* isopentenyl-phosphate kinase mutant gene.

Competent *Saccharomyces cerevisiae* InvSc1 (MATa his3D1 leu2 trp1-289 ura3-52) (Invitrogen) cells are transformed sequentially with the expression vectors and then plated on minimal agar plates (1.7 g/L yeast nitrogen base without amino acids or ammonium sulfate (DIFCO), 5 g/L $(NH_4)_2SO_4$, 20 g/L glucose, 20 g/L agar containing amino acids for selection based on uracil and trytophan prototrophy. Transformants are picked and grown for 24 hours in uracil- and tryptophan-deficient minimal medium. Plasmid DNA is isolated from the transformants and analyzed by restriction digestion analysis to confirm identity.

A successful transformant is used to inoculate 2 mL of uracil-deficient minimal medium and is grown overnight at 30° C. in an orbital shaker. A 500 µL aliquot of this culture is used to inoculate 50 mL of YEPD medium (Wobbe, in Current Protocols in Molecular Biology, Supplement 34:13.0.1-13.13.9 (Wiley, 1996)) (10 g/L yeast extract, 20 g/L peptone, 20 g/L glucose), and the culture is grown at 30° C. in a shaker in the presence of olivetolic acid (10 grams/L), prenol (10 grams/L) and isoprenol (10 grams/L).

Cells are collected by centrifugation of 500 µL aliquots of the culture taken after 24 and, 48 and 72 hours of growth and lysed by boiling in 50 µL of 2×SDS gel loading buffer for about 2 minutes. The cell lysates are analyzed by loading onto 12% SDS-PAGE gels. Bands corresponding to the expected size of the encoded enzymes are observed.

CBGA isolated from the yeast supernatants and associated with the spun yeast cells are identified by comparison with a known standard on thin layer chromatography (TLC) plates, and by HPLC.

Example 2—Production of CBDA Directly in *S. cerevisiae*

The plasmids described above in EXAMPLE 1 are sequentially transformed into the yeast strain *Saccharomyces cerevisiae* InvSc1 (MATa his3D1 leu2 trp1-289 ura3-52) (Invitrogen), into which had been transformed previously, by genomic integration, a DNA construct encoding both the *C. sativa* CBDA synthase and the human catalase genes, each fused to and under the control of the GPD promoter.

The transformed yeast cells are grown in shake flasks containing YEPD media with 2% glucose for 48 and 72 hours. The media also contains olivetolic acid (10 grams/L), prenol (10 grams/L) and isoprenol (10 grams/L). In this experiment, the fed olivetolic acid was derived from supernatants of yeast cells transformed with yeast expression vectors encoding the *C. sativa* olivetolic acid synthase gene and a truncated *C. sativa* olivetolic acid cyclase gene. The olivetolic acid-containing media was concentrated prior to using as a substrate for the above experiment, by evaporation.

CBDA isolated from the yeast supernatants and associated with the spun yeast cells are identified by comparison with a known standard on thin layer chromatography (TLC) plates, and by HPLC.

Example 3—Chemical Conversion of $\Delta^9$-THCA to CBN Directly in *S. cerevisiae*

One mL of $\Delta^9$-THCA-containing yeast cells with a concentration of $\Delta^9$-THCA of ~7 mg/mL was spun down, and the resulting pellet suspended in 500 uL of 95% ethanol. The solvent was evaporated and the resulting residue heated to 120° C. Samples were taken periodically and analysed by reversed-phase HPLC monitoring the rate of conversion of THCA to THC to cannabinol (CBN). The time to completion of a control reaction without yeast cells present was approximately 40 hours although, surprisingly, in the presence of yeast cells, the time to completion was less than 20 hours.

Example 4—Chemical Conversion of CBD to CBDN Directly in *S. cerevisiae*

One mL of CBD-containing yeast cells with a concentration of CBD of ~6 mg/mL was spun down, and the resulting pellet suspended in 500 uL of 95% ethanol. The solvent was evaporated and the resulting residue heated to 120° C. Samples were taken periodically and analysed by reversed-phase HPLC monitoring the rate of conversion of CBD to cannabinodiol (CBDN). The time to 50% completion of this reaction, both with and without yeast cells as a control, was approximately 70 hours.

Example 5—Decarboxylation of CBDA to CBD Directly in S. cerevisiae

One mL of CBDA-containing yeast cells with a concentration of CBDA of ~7 mg/mL was spun down, and the resulting pellet suspended in 500 uL of 95% ethanol. The solvent was evaporated and the resulting residue heated to 100° C. Samples were taken periodically and analysed by reversed-phase HPLC monitoring the rate of decarboxylation to CBD. The half-life of this decarboxylation reaction, with or without yeast cells present as a control, was approximately 45 minutes.

Example 6—Biosynthesis of Olivetolic Acid and its Analogs in Yeast

Figure 5:
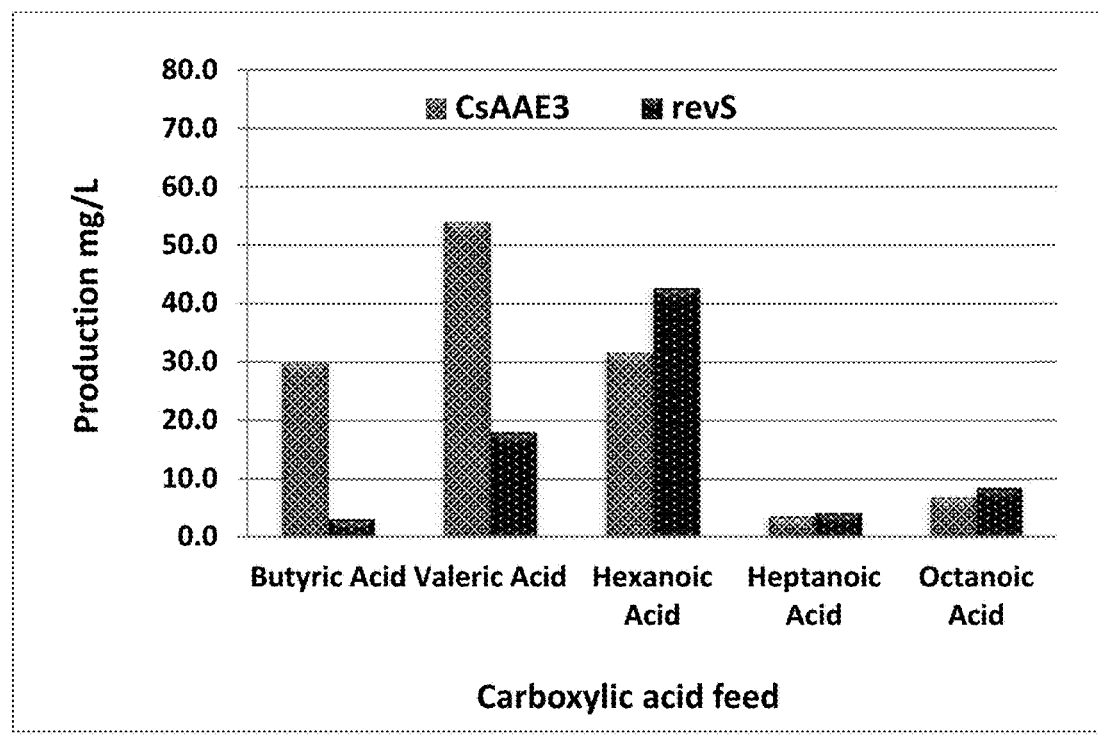
FIG. 5 depicts the production of polyketide cannabinoid precursors in shake-flask cultures by feeding of aliphatic carboxylic acids to *Saccharomyces* yeast strains expressing the acyl-CoA synthetases *C. sativa* CsAAE3 and the middle chain fatty acyl-CoA ligase revS from *Streptomyces* sp. SN-593.

S. cerevisiae yeast strains containing one of the acyl-CoA synthetase genes CsAAE1, CsAAE3, or the middle chain fatty acyl-CoA ligase revS gene from Streptomyces sp. SN-593 were co-transformed into yeast using the Ura3 and Leu2 selectable markers on plasmids that contained the C. sativa olivetolic acid synthase and cyclase genes, driven by the ADH2 promoter and separated by the yeast p150 internal ribosome entry site (IRES) to generate a dicistronic mRNA, were grown in 25 ml shake-flask cultures in rich media with 2% glucose. After 30 hours, the yeast cultures were fed with various aliphatic carboxylic acids and the media was sampled at various time-points by reversed-phase HPLC. As shown in FIG. 5, all acids tested gave products in varying yields. The hexanoic acid feed gave high yields of olivetolic acid with a side-production of low levels of olivetol.

FIG. 5 depicts the production of polyketide cannabinoid precursors olivetolic and divarinic acids and analogs in 25 mL shake-flask cultures by feeding of aliphatic carboxylic acids to Saccharomyces yeast strains expressing the acyl-CoA synthetases C. sativa CsAAE3 and the middle chain fatty acyl-CoA ligase revS from Streptomyces sp. SN-593 for 60 hours. Since one carbon enters the aromatic polyketide ring, the side chain is one carbon shorter than the carboxylic acid substrate. Thus, divarinic and olivetolic acids are made from butyric (butanoic) and hexanoic acids respectively, resulting in propyl- and pentyl-side chains. Results with a further three carboxylic acids, valeric (pentanoic), heptanoic and octanoic acids are also shown. As shown in FIG. 5, all acids tested gave products in varying yields. The hexanoic acid feed gave high yields of olivetolic acid with a side-production of low levels of olivetol.

Example 7—Use of Ubiquitin Fusion Technology to Improve Cyclase Activities

The experiments of EXAMPLE 6 were repeated with a co-transformed plasmid that also encoded a human ubiquitin gene fused in-frame to the 5'-end of the cyclase gene, or a truncated cyclase gene. Upon hexanoic acid feeding and HPLC analysis of the media, high levels of olivetolic acid were observed.

Example 8—Fermentations with Varying Feed Protocols

Multiple 7.5 liter fermenters (Eppendorf) were run at an initial working volume of three liters, and with standard fed-batch glucose/media feed protocols in order to maximize production of olivetolic acid with simultaneous glucose and hexanoic acid feeding. The strains described in EXAMPLE 6 were grown to 350 mL overnight in defined uracil and leucine deficient media prior to inoculation into the fermenter, containing 2×YEP with 1.25% glucose. Agitation was set at 400-600 rpm, with aeration at a 1-2 vvm (liters of air/per liter of media/minute). Feeding with 2×YEP/20% glucose was controlled such that the feed matched the yeast cell growth-rate with no build-up of glucose or ethanol. At 30 hours post-inoculation, 3 mL of hexanoic acid was added to the leftover feeding medium, providing a hexanoic acid feeding rate of about 48 uL/L/hr. The fermentations and feeding were continued to 54 hours post-inoculation at which point, a further 2.5 mL of hexanoic acid was added. At 72 hours, the fermentations were concluded and the media analyzed by HPLC. In typical runs, 160 mg/L of olivetolic acid and 16 mg/L of olivetol were produced. The above fed-batch fermentation protocol was repeated using valeric (pentanoic) and butyric (butanoic) acids to give 2-butyl-4,6-dihydroxybenzoic acid (i.e., the butyl-containing analog of olivetolic acid) and divarinic acid, respectively.

In further fermentations, hexanoic acid was added as part of the media/glucose feed and the addition was controlled to be either linear or logarithmic. Also, pH was controlled such that the production of olivetol was reduced to trace levels.

Example 9—Varying Fermentation pH to Reduce Formation of Olivetol Side Product

Figure 6:
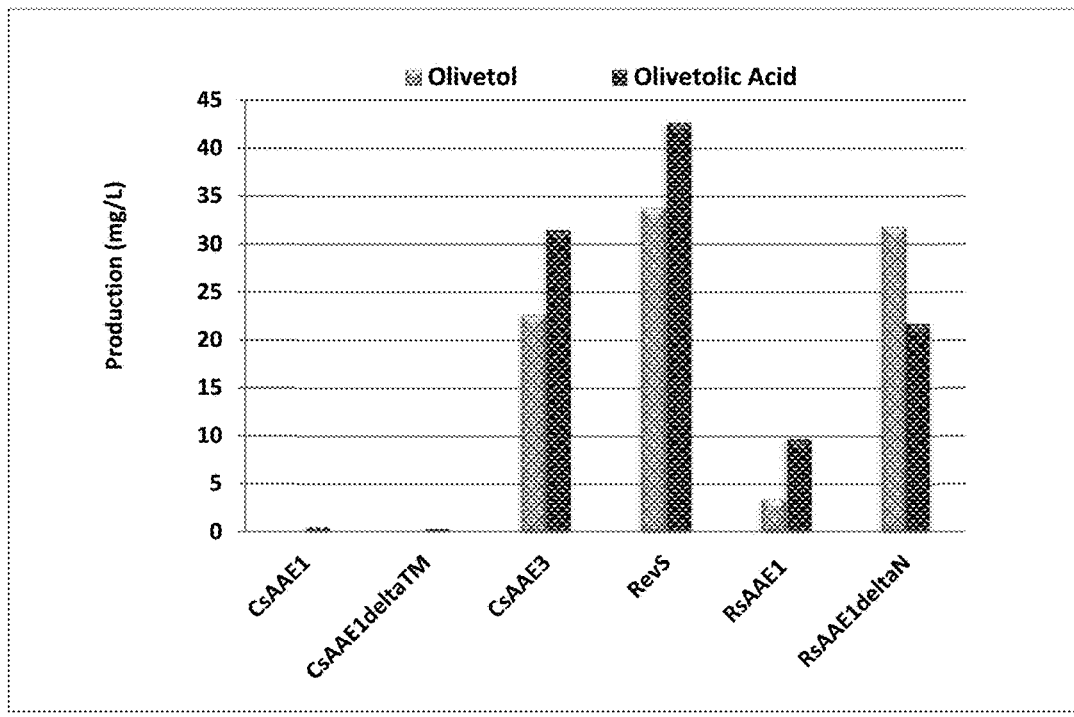
FIG. 6 depicts the production of olivetol and olivetolic acid upon feeding various yeast shake-flask cultures with hexanoic acid. In addition to being transformed with plasmids that contained OAS and OAC genes, the individual strains were also transformed with genes for CsAAE1 (lane 1), CsAAE1 with a transmembrane domain deletion (lane2), CsAAE3 (lane 3), revS (lane 4), the 647 amino acid *R. solanacearum* acyl-CoA synthase RsAAE1 (lane 5) and the C-terminal 415 amino acids of the *R. solanacearum* acyl-CoA synthase RsAAE1 (lane 6).
Figure 7:
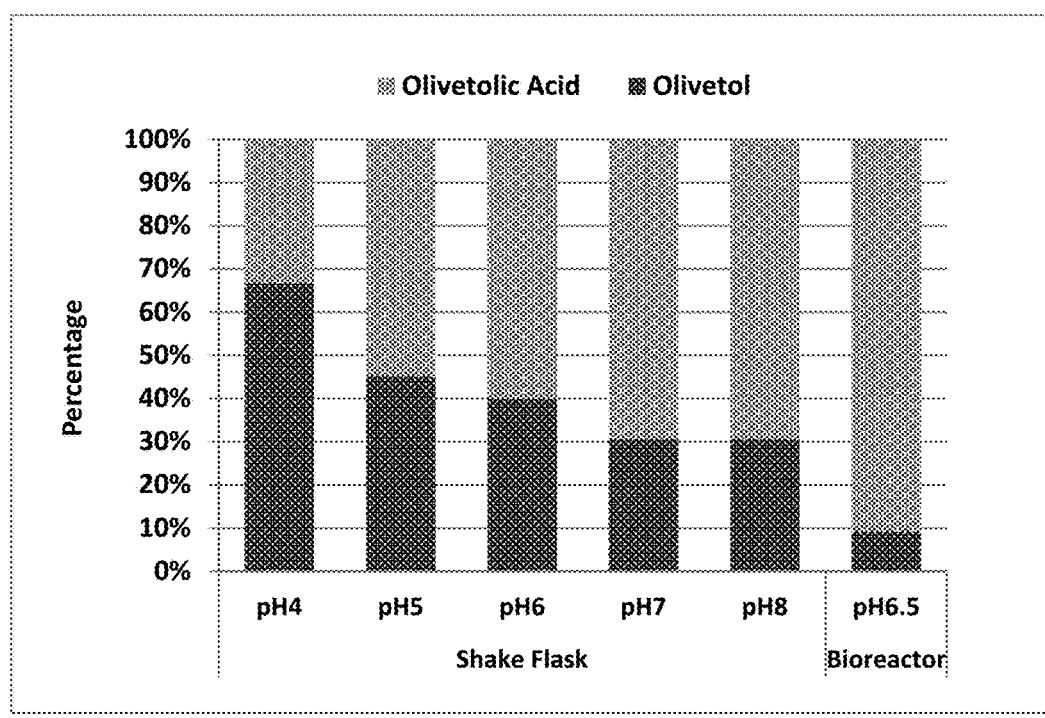
FIG. 7 depicts the influence of pH on olivetolic acid versus olivetol expression in shake-flask experiments (lanes 1-5), and the effect of increased aeration at pH6.5 in a 3-liter fermentation (lane 6). pH on olivetolic acid expression.

The shake-flask protocols described in EXAMPLE 6 were repeated with various media pHs held constant by buffering, within each flask. It was found that higher pHs led to reduced formation of the olivetol side-product. Also, in a fermentation conducted at pH 6.5, a ratio of olivetolic acid/olivetol of greater than 9:1 was observed. (FIG. 6, column 6).

Example 10—Chemical Geranylation of Olivetolic Acid to CBGA in Dried Yeast Cells To a suspension of 55 mg of thoroughly dried yeast cells containing 17.4 mg of olivetolic acid in 0.25 mL of toluene was added 2.6 mg of p-toluenesulphonic acid and 18 μL of geraniol. The suspension was heated to 60° C. and monitored by reversed-phase HPLC (Kinetex 5 μm-XB, 50×4.6 mm, 100A, linear gradient of 20% 50 mM ammonium formate/acetonitrile to 100% acetonitrile over 6 min. at 2.5 mL/min.). CBGA was identified by comparison with a CBGA standard matching elution time and UV fingerprint trace (200-400 nm) and reached its maximal yield after approximately 50 minutes.

Example 11—Chemical Conversion of Olivetolic Acid to CBCA/CBC in Dried Yeast Cells To a suspension of 55 mg of thoroughly dried yeast cells containing 11 mg of olivetolic acid in 1.0 ml of toluene was added 0.011 mL of citral and 0.33 uL of N,N dimethylethylene diamine. The suspension was heated to 60° C. and monitored by reversed-phase HPLC (Kinetex 5 um-XB, 50×4.6 mm, 100A, linear gradient of 80% 50 mM ammonium formate (pH 5)/acetonitrile to 100% acetonitrile over 6 min. at 2.5 mls/min. or 80% water/acetonitrile/0.1% TFA to 100% acetonitrile/0.1% TFA). Both CBCA and CBC were identified by comparison with the published UV fingerprint trace (200-400 nm) matching exactly in either acidic gradient or pH5 gradient, and further by LC-MS, where CBCA gives a M-H=356.95, based on molecular formula $C_{22}H_{30}O_4$ calculates for an exact mass of 357.2, and CBC which gives a M-H=313.05, based on molecular formula $C_{21}H_{30}O_2$ calculates for an exact mass of 314.2.

Example 12—Chemical or Enzymatic Decarboxylation of CBGA

Yeast strain y2-pBM560U (3 mL) that contained a plasmid expressing the *Aspergillus nidulans* orsB decarboxylase gene, under the control of the ADH2 promoter, was cultured overnight in defined uracil-deficient media. 3 mL of the culture was inoculated into multiple flasks containing 27 mls of YPD media with 2% glucose. The cultures were grown for a further 30 hours at 30° C. The cell cultures were then split to perform two types of experiment, a) in vivo decarboxylation of exogenously added OA, OSA, CBGA and CBDA and b) decarboxylation of exogenously OA, OSA, CBGA and CBDA that was added to yeast cells that had been lysed using glass beads in TE (10 mM Tris Cl+1 mM EDTA; pH8) buffer. In each experiment, the expressed orsB decarboxylase was found to decarboxylate OSA rapidly. Unexpectedly, orsB decarboxylase was also found to be able to decarboxylate the acidic cannabinoids, as monitored by HPLC.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

ILLUSTRATIVE SEQUENCES

---

SEQ ID NO: 1 Illustrative RevS polypeptide
sequence GenBank BAK64635.1
MELALPAELAPTLPEALRLRSEQQPDTVAYVFLRDGETPEETLTYGRLDR
AARARAAALEAAGLAGGTAVLLYPSGLEFVAALLGCMYAGTAGAPVQVPT
RRRGMERARRIADDAGAKTILTTTAVKREVEEHFADLLTGLTVIDTESLP
DVPDDAPAVRLPGPDDVALLQYTSGSTGDPKGVEVTHANFRANVAETVEL
WPVRSDGTVVNWLPLFHDMGLMFGVVMPLFTGVPAYLMAPQSFIRRPARW
LEAISRFRGTHAAAPSFAYELCVRSVADTGLPAGLDLSSWRVAVNGAEPV
RWTAVADFTEAYAPAGFRPQAMCPGYGLAENTLKLSGSPEDRPPTLLRAD
AAALQDGRVVPLTGPGTDGVRLVGSGVTVPSSRVAVVDPGTGTEQPAGRV
GEIWINGPCVARGYHGRPAESAESFGARIAGQEARGTWLRTGDLGFLHDG
EVFVAGRLKDVVIHQGRNFYPQDIELSAEVSDRALHPNCAAAFALDDGRT
ERLVLLVEADGRALRNGGADALRARVHDAVWDRQRLRIDEIVLLRRGALP
KTSSGKVQRRLARSRYLDGEFGPAPAREA SEQ ID NO: 2 Illustrative *Cannabis sativa* CSAAE3
polypeptide sequence; GenBank AFD33347.1
MEKSGYGRDGIYRSLRPPLHLPNNNNLSMVSFLFRNSSSYPQKPALIDSE
TNQILSFSHFKSTVIKVSHGFLNLGIKKNDVVLIYAPNSIHFPVCFLGII
ASGAIATTSNPLYTVSELSKQVKDSNPKLIITVPQLLEKVKGFNLPTILI
GPDSEQESSSDKVMTFNDLVNLGGSSGSEFPIVDDFKQSDTAALLYSSGT
TGMSKGVVLTHKNFIASSLMVTMEQDLVGEMDNVFLCFLPMFHVFGLAII
TYAQLQRGNTVISMARFDLEKMLKDVEKYKVTHLWVVPPVILALSKNSMV
KKFNLSSIKYIGSGAAPLGKDLMEECSKVVPYGIVAQGYGMTETCGIVSM
EDIRGGKRNSGSAGMLASGVEAQIVSVDTLKPLPPNQLGEIWVKGPNMMQ
GYFNNPQATKLTIDKKGWVHTGDLGYFDEDGHLYVVDRIKELIKYKGFQV
APAELEGLLVSHPEILDAVVIPFPDAEAGEVPVAYVVRSPNSSLTENDVK
KFIAGQVASFKRLRKVTFINSVPKSASGKILRRELIQKVRSNM SEQ ID NO: 3 Illustrative *Cannabis sativa* CSAAE1
polypeptide sequence; GenBank AFD33345.1 A
transmembrane domain is underlined
MGKNYKSLDSVVASDFIALGITSEVAETLHGRLAEIVCNYGAATPQTWIN
IANHILSPDLPFSLHQMLFYGCYKDFGPAPPAWIPDPEKVKSTNLGALLE
KRGKEFLGVKYKDPISSFSHFQEFSVRNPEVYWRTVLMDEMKISFSKDPE
CILRRDDINNPGGSEWLPGGYLNSAKNCLNVNSNKKLNDTMIVWRDEGND
DLPLNKLTLDQLRKRVWLVGYALEEMGLEKGCAIAIDMPMHVDA<u>VVIYLA
IVLAGYVVVSIADSFSAPEISTRLRLSKAKAIFTQDHIIRGKKRI</u>PLYSR
VVEAKSPMAIVIPCSGSNIGAELRDGDISWDYFLERAKEFKNCEFTAREQ
PVDAYTNILFSSGTTGEPKAIPWTQATPLKAAADGWSHLDIRKGDVIVWP
TNLGWMMGPWLVYASLLNGASIALYNGSPLVSGFAKFVQDAKVTMLGVVP
SIVRSWKSTNCVSGYDWSTIRCFSSSGEASNVDEYLWLMGRANYKPVIEM
CGGTEIGGAFSAGSFLQAQSLSSFSSQCMGCTLYILDKNGYPMPKNKPGI
GELALGPVMFGASKTLLNGNHHDVYFKGMPTLNGEVLRRHGDIFELTSNG
YYHAHGRADDTMNIGGIKISSIEIERVCNEVDDRVFETTAIGVPPLGGGP
EQLVIFFVLKDSNDTTIDLNQLRLSFNLGLQKKLNPLFKVTRVVPLSSLP
RTATNKIMRRVLRQQFSHFE SEQ ID NO: 4 Illustrative olivetolic acid synthase
polypeptide sequence; UniProtKB/Swiss-Prot:
B1Q2B6.1
MNHLRAEGPASVLAIGTANPENILLQDEFPDYYFRVTKSEHMTQLKEKFR
KICDKSMIRKRNCFLNEEHLKQNPRLVEHEMQTLDARQDMLVVEVPKLGK
DACAKAIKEWGQPKSKITHLIFTSASTTDMPGADYHCAKLLGLSPSVKRV
MMYQLGCYGGGTVLRIAKDIAENNKGARVLAVCCDIMACLFRGPSESDLE
LLVGQAIFGDGAAAVIVGAEPDESVGERPIFELVSTGQTILPNSEGTIGG
HIREAGLIFDLHKDVPMLISNNIEKCLIEAFTPIGISDWNSIFWITHPGG
KAILDKVEEKLHLKSDKFVDSRHVLSEHGNMSSSTVLFVMDELRKRSLEE
GKSTTGDGFEWGVLFGFGPGLTVERVVVRSVPIKY SEQ ID NO: 5 Illustrative olivetolic acid cyclase
polypeptide sequence; UniProtKB/Swiss-Prot:
I6WU39.1
MAVKHLIVLKFKDEITEAQKEEFFKTYVNLVNIIPAMKDVYWGKDVTQKN
KEEGYTHIVEVTFESVETIQDYIIHPAHVGFGDVYRSFWEKLLIFDYTPR
K SEQ ID NO: 6 olivetolic acid cyclase polypeptide
sequence lacking the N-terminal methionine and C-
terminal lysine relative to SEQ ID NO:5
AVKHLIVLKFKDEITEAQKEEFFKTYVNLVNIIPAMKDVYWGKDVTQKNK
EEGYTHIVEVTFESVETIQDYIIHPAHVGFGDVYRSFWEKLLIFDYTPR SEQ ID NO: 7 Truncated version of cyclase, 95 aa,
lacking the N-terminal methionine and five amino
acid sequence YTPRK at the C-terminal end relative
to SEQ ID NO: 5
AVKHLIVLKFKDEITEAQKEEFFKTYVNLVNIIPAMKDVYWGKDVTQKNK
EEGYTHIVEVTFESVETIQDYIIHPAHVGFGDVYRSFWEKLLIFD SEQ ID NO :8 Amino acid sequence of 415-amino acid
C-terminal domain of *Ralstonia solanacearum* acyl-
CoA synthase
MAFNERVVDWQQVAGAQPDASPERMSADDPFMIIYTSGTTGKPKGTVHT
HGSFPMKIAHDSAIHFNVSPKDVFCWPADMGWVAGTLVMSCALLRGATL
VCYDGAPDFPDWSRMSRLIERHRVTHFGSAPTLIRGLASNEAIATQGDV
SSVKLLITAGEGIDPEHFLWFQKAFGGGHRPVINYTGGTEVSGALLSSV
VIKPISPAGFNTASPGVATDVVDAEGHSVTGEVGELAIRKPFIGMTRSF
WQDDERYLDSYWRTIPGIWVHGDLAMRREDGMWFMMGRSDDTIKLAGKR
LGPAEIEDVLLELPEIAEAAAIGVEDPVKGQKLVVFVVASKASTASADA
LASVIGKHVDLRLGRPFRPSVVHVVAQLPKTRSSKIMRRVIRSVYTGKP
AGDLSSLDNPLALDEIRSAAAVS

What is claimed is:

1. A modified recombinant yeast cell comprising: (i) a first exogenous polynucleotide that encodes an acyl-CoA synthetase that converts an aliphatic carboxylic acid to an acyl CoA thioester, wherein the acyl-CoA synthetase polypeptide comprises an amino acid sequence having at least 95% identity to SEP ID NO: 1, (ii) a second exogenous polynucleotide that encodes an olivetolic acid synthase polypeptide comprising an amino acid sequence having at least 95% identity to SEP ID NO:4, (iii) and a third exogenous polynucleotide that encodes a 2-alkyl-4,6-dihydroxybenzoic acid cyclase polypeptide comprising an amino acid sequence having at least 95% identity to SEP ID NO:5, 6, or 7, wherein the second and third exogenous polynucleotide are expressed as a dicistronic mRNA.

2. The modified recombinant yeast cell of claim 1, which is a cell selected from the group consisting of *Saccharomyces cerevisiae, Kluyveromyces lactis, Kluyveromyces marxianus, Pichia pastoris, Yarrowia lipolytica*, and *Hansenula polymorpha*.

3. The modified recombinant yeast cell of claim 1, wherein the acyl-CoA synthetase polypeptide comprises the amino acid sequence of SEQ ID NO: 1.

4. The modified recombinant yeast cell of claim 1, wherein the olivetolic acid synthase polypeptide comprises the amino acid sequence of SEQ ID NO:4.

5. The modified recombinant yeast cell of claim 1, wherein the 2-alkyl-4,6-dihydroxybenzoic acid cyclase is a truncated olivetolic acid cyclase polypeptide of amino acid sequence SEQ ID NO:7.

6. The modified recombinant yeast cell of claim 1, wherein the acyl-CoA synthetase polypeptide comprises the amino acid sequence of SEQ ID NO:1, the olivetolic acid synthase polypeptide comprises the amino acid sequence of SEQ ID NO:4, and the 2-alkyl-4,6-dihydroxybenzoic acid cyclase polypeptide comprises the amino acid sequence of SEQ ID NO:5, 6, or 7.

7. The modified recombinant yeast cell of claim 6, wherein the 2-alkyl-4,6-dihydroxybenzoic acid cyclase is a truncated olivetolic acid cyclase polypeptide of amino acid sequence SEQ ID NO:7.

8. The modified recombinant yeast cell of claim 7, wherein expression of the dicistronic mRNA is driven by a yeast alcohol dehydrogenase-2 promoter.

9. The modified recombinant yeast cell of claim 1, wherein the second and third exogenous polynucleotides are present in an autonomously replicating expression vector.

10. A cell culture comprising a plurality of the modified recombinant yeast cell of claim 1 and a cell culture medium.

11. The cell culture of claim 10, wherein the cell culture medium comprises hexanoic acid.

12. A method of producing olivetolic acid, the method comprising culturing the cell culture of claim 11 under conditions in which olivetolic acid is produced.

13. The method of claim 12, wherein the cell culture is grown at a pH from 6.0 to 8.0.

* * * * *

UNITED STATES PATENT AND TRADEMARK OFFICE
CERTIFICATE OF CORRECTION

PATENT NO. : 10,837,031 B2  
APPLICATION NO. : 15/976755  
DATED : November 17, 2020  
INVENTOR(S) : Philip J. Barr, Charles K. Marlowe and Jianping Sun Page 1 of 1

It is certified that error appears in the above-identified patent and that said Letters Patent is hereby corrected as shown below:

In the Claims

In Column 45, Line 61, Claim 1, delete "SEP" and replace with --SEQ--

In Column 45, Line 64, Claim 1, delete "SEP" and replace with --SEQ--

In Column 45, Line 67, Claim 1, delete "SEP" and replace with --SEQ--

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 9

<210> SEQ ID NO 1
<211> LENGTH: 579
<212> TYPE: PRT
<213> ORGANISM: Artificial Sequence
<220> FEATURE:
<223> OTHER INFORMATION: synthetic Illustrative RevS polypeptide sequence

<400> SEQUENCE: 1

```
Met Glu Leu Ala Leu Pro Ala Glu Leu Ala Pro Thr Leu Pro Glu Ala
1               5                   10                  15

Leu Arg Leu Arg Ser Glu Gln Gln Pro Asp Thr Val Ala Tyr Val Phe
            20                  25                  30

Leu Arg Asp Gly Glu Thr Pro Glu Glu Thr Leu Thr Tyr Gly Arg Leu
        35                  40                  45

Asp Arg Ala Ala Arg Ala Arg Ala Ala Ala Leu Glu Ala Ala Gly Leu
    50                  55                  60

Ala Gly Gly Thr Ala Val Leu Leu Tyr Pro Ser Gly Leu Glu Phe Val
65                  70                  75                  80

Ala Ala Leu Leu Gly Cys Met Tyr Ala Gly Thr Ala Gly Ala Pro Val
                85                  90                  95

Gln Val Pro Thr Arg Arg Arg Gly Met Glu Arg Ala Arg Arg Ile Ala
            100                 105                 110

Asp Asp Ala Gly Ala Lys Thr Ile Leu Thr Thr Thr Ala Val Lys Arg
        115                 120                 125

Glu Val Glu Glu His Phe Ala Asp Leu Leu Thr Gly Leu Thr Val Ile
    130                 135                 140

Asp Thr Glu Ser Leu Pro Asp Val Pro Asp Asp Ala Pro Ala Val Arg
145                 150                 155                 160

Leu Pro Gly Pro Asp Asp Val Ala Leu Leu Gln Tyr Thr Ser Gly Ser
                165                 170                 175

Thr Gly Asp Pro Lys Gly Val Glu Val Thr His Ala Asn Phe Arg Ala
            180                 185                 190

Asn Val Ala Glu Thr Val Glu Leu Trp Pro Val Arg Ser Asp Gly Thr
        195                 200                 205

Val Val Asn Trp Leu Pro Leu Phe His Asp Met Gly Leu Met Phe Gly
    210                 215                 220

Val Val Met Pro Leu Phe Thr Gly Val Pro Ala Tyr Leu Met Ala Pro
225                 230                 235                 240

Gln Ser Phe Ile Arg Arg Pro Ala Arg Trp Leu Glu Ala Ile Ser Arg
                245                 250                 255

Phe Arg Gly Thr His Ala Ala Ala Pro Ser Phe Ala Tyr Glu Leu Cys
            260                 265                 270

Val Arg Ser Val Ala Asp Thr Gly Leu Pro Ala Gly Leu Asp Leu Ser
        275                 280                 285

Ser Trp Arg Val Ala Val Asn Gly Ala Glu Pro Val Arg Trp Thr Ala
    290                 295                 300

Val Ala Asp Phe Thr Glu Ala Tyr Ala Pro Ala Gly Phe Arg Pro Gln
305                 310                 315                 320

Ala Met Cys Pro Gly Tyr Gly Leu Ala Glu Asn Thr Leu Lys Leu Ser
                325                 330                 335

Gly Ser Pro Glu Asp Arg Pro Pro Thr Leu Leu Arg Ala Asp Ala Ala
            340                 345                 350
```

```
Ala Leu Gln Asp Gly Arg Val Val Pro Leu Thr Gly Pro Gly Thr Asp
            355                 360                 365

Gly Val Arg Leu Val Gly Ser Gly Val Thr Val Pro Ser Ser Arg Val
    370                 375                 380

Ala Val Val Asp Pro Gly Thr Gly Thr Glu Gln Pro Ala Gly Arg Val
385                 390                 395                 400

Gly Glu Ile Trp Ile Asn Gly Pro Cys Val Ala Arg Gly Tyr His Gly
            405                 410                 415

Arg Pro Ala Glu Ser Ala Glu Ser Phe Gly Ala Arg Ile Ala Gly Gln
            420                 425                 430

Glu Ala Arg Gly Thr Trp Leu Arg Thr Gly Asp Leu Gly Phe Leu His
            435                 440                 445

Asp Gly Glu Val Phe Val Ala Gly Arg Leu Lys Asp Val Val Ile His
            450                 455                 460

Gln Gly Arg Asn Phe Tyr Pro Gln Asp Ile Glu Leu Ser Ala Glu Val
465                 470                 475                 480

Ser Asp Arg Ala Leu His Pro Asn Cys Ala Ala Ala Phe Ala Leu Asp
            485                 490                 495

Asp Gly Arg Thr Glu Arg Leu Val Leu Leu Val Glu Ala Asp Gly Arg
            500                 505                 510

Ala Leu Arg Asn Gly Gly Ala Asp Ala Leu Arg Ala Arg Val His Asp
            515                 520                 525

Ala Val Trp Asp Arg Gln Arg Leu Arg Ile Asp Glu Ile Val Leu Leu
            530                 535                 540

Arg Arg Gly Ala Leu Pro Lys Thr Ser Ser Gly Lys Val Gln Arg Arg
545                 550                 555                 560

Leu Ala Arg Ser Arg Tyr Leu Asp Gly Glu Phe Gly Pro Ala Pro Ala
                565                 570                 575

Arg Glu Ala

<210> SEQ ID NO 2
<211> LENGTH: 543
<212> TYPE: PRT
<213> ORGANISM: Cannabis sativa

<400> SEQUENCE: 2

Met Glu Lys Ser Gly Tyr Gly Arg Asp Gly Ile Tyr Arg Ser Leu Arg
1               5                   10                  15

Pro Pro Leu His Leu Pro Asn Asn Asn Leu Ser Met Val Ser Phe
                20                  25                  30

Leu Phe Arg Asn Ser Ser Ser Tyr Pro Gln Lys Pro Ala Leu Ile Asp
            35                  40                  45

Ser Glu Thr Asn Gln Ile Leu Ser Phe Ser His Phe Lys Ser Thr Val
    50                  55                  60

Ile Lys Val Ser His Gly Phe Leu Asn Leu Gly Ile Lys Lys Asn Asp
65                  70                  75                  80

Val Val Leu Ile Tyr Ala Pro Asn Ser Ile His Phe Pro Val Cys Phe
                85                  90                  95

Leu Gly Ile Ile Ala Ser Gly Ala Ile Ala Thr Thr Ser Asn Pro Leu
            100                 105                 110

Tyr Thr Val Ser Glu Leu Ser Lys Gln Val Lys Asp Ser Asn Pro Lys
    115                 120                 125

Leu Ile Ile Thr Val Pro Gln Leu Leu Glu Lys Val Lys Gly Phe Asn
    130                 135                 140
```

Leu Pro Thr Ile Leu Ile Gly Pro Asp Ser Glu Gln Glu Ser Ser Ser
145                 150                 155                 160

Asp Lys Val Met Thr Phe Asn Asp Leu Val Asn Leu Gly Gly Ser Ser
            165                 170                 175

Gly Ser Glu Phe Pro Ile Val Asp Asp Phe Lys Gln Ser Asp Thr Ala
            180                 185                 190

Ala Leu Leu Tyr Ser Ser Gly Thr Thr Gly Met Ser Lys Gly Val Val
            195                 200                 205

Leu Thr His Lys Asn Phe Ile Ala Ser Ser Leu Met Val Thr Met Glu
210                 215                 220

Gln Asp Leu Val Gly Glu Met Asp Asn Val Phe Leu Cys Phe Leu Pro
225                 230                 235                 240

Met Phe His Val Phe Gly Leu Ala Ile Ile Thr Tyr Ala Gln Leu Gln
            245                 250                 255

Arg Gly Asn Thr Val Ile Ser Met Ala Arg Phe Asp Leu Glu Lys Met
            260                 265                 270

Leu Lys Asp Val Glu Lys Tyr Lys Val Thr His Leu Trp Val Val Pro
            275                 280                 285

Pro Val Ile Leu Ala Leu Ser Lys Asn Ser Met Val Lys Lys Phe Asn
290                 295                 300

Leu Ser Ser Ile Lys Tyr Ile Gly Ser Gly Ala Ala Pro Leu Gly Lys
305                 310                 315                 320

Asp Leu Met Glu Glu Cys Ser Lys Val Val Pro Tyr Gly Ile Val Ala
            325                 330                 335

Gln Gly Tyr Gly Met Thr Glu Thr Cys Gly Ile Val Ser Met Glu Asp
            340                 345                 350

Ile Arg Gly Gly Lys Arg Asn Ser Gly Ser Ala Gly Met Leu Ala Ser
            355                 360                 365

Gly Val Glu Ala Gln Ile Val Ser Val Asp Thr Leu Lys Pro Leu Pro
            370                 375                 380

Pro Asn Gln Leu Gly Glu Ile Trp Val Lys Gly Pro Asn Met Met Gln
385                 390                 395                 400

Gly Tyr Phe Asn Asn Pro Gln Ala Thr Lys Leu Thr Ile Asp Lys Lys
            405                 410                 415

Gly Trp Val His Thr Gly Asp Leu Gly Tyr Phe Asp Glu Asp Gly His
            420                 425                 430

Leu Tyr Val Val Asp Arg Ile Lys Glu Leu Ile Lys Tyr Lys Gly Phe
            435                 440                 445

Gln Val Ala Pro Ala Glu Leu Glu Gly Leu Leu Val Ser His Pro Glu
450                 455                 460

Ile Leu Asp Ala Val Val Ile Pro Phe Pro Asp Ala Glu Ala Gly Glu
465                 470                 475                 480

Val Pro Val Ala Tyr Val Val Arg Ser Pro Asn Ser Ser Leu Thr Glu
            485                 490                 495

Asn Asp Val Lys Lys Phe Ile Ala Gly Gln Val Ala Ser Phe Lys Arg
            500                 505                 510

Leu Arg Lys Val Thr Phe Ile Asn Ser Val Pro Lys Ser Ala Ser Gly
            515                 520                 525

Lys Ile Leu Arg Arg Glu Leu Ile Gln Lys Val Arg Ser Asn Met
            530                 535                 540

<210> SEQ ID NO 3
<211> LENGTH: 720
<212> TYPE: PRT

<213> ORGANISM: Cannabis sativa
<220> FEATURE:
<221> NAME/KEY: TRANSMEM
<222> LOCATION: (245)..(267)

<400> SEQUENCE: 3

Met Gly Lys Asn Tyr Lys Ser Leu Asp Ser Val Ala Ser Asp Phe
1               5                   10                  15

Ile Ala Leu Gly Ile Thr Ser Glu Val Ala Glu Thr Leu His Gly Arg
            20                  25                  30

Leu Ala Glu Ile Val Cys Asn Tyr Gly Ala Ala Thr Pro Gln Thr Trp
                35                  40                  45

Ile Asn Ile Ala Asn His Ile Leu Ser Pro Asp Leu Pro Phe Ser Leu
    50                  55                  60

His Gln Met Leu Phe Tyr Gly Cys Tyr Lys Asp Phe Gly Pro Ala Pro
65              70                  75                  80

Pro Ala Trp Ile Pro Asp Pro Glu Lys Val Lys Ser Thr Asn Leu Gly
                85                  90                  95

Ala Leu Leu Glu Lys Arg Gly Lys Glu Phe Leu Gly Val Lys Tyr Lys
            100                 105                 110

Asp Pro Ile Ser Ser Phe Ser His Phe Gln Glu Phe Ser Val Arg Asn
        115                 120                 125

Pro Glu Val Tyr Trp Arg Thr Val Leu Met Asp Glu Met Lys Ile Ser
    130                 135                 140

Phe Ser Lys Asp Pro Glu Cys Ile Leu Arg Arg Asp Asp Ile Asn Asn
145                 150                 155                 160

Pro Gly Gly Ser Glu Trp Leu Pro Gly Gly Tyr Leu Asn Ser Ala Lys
                165                 170                 175

Asn Cys Leu Asn Val Asn Ser Asn Lys Lys Leu Asn Asp Thr Met Ile
            180                 185                 190

Val Trp Arg Asp Glu Gly Asn Asp Asp Leu Pro Leu Asn Lys Leu Thr
        195                 200                 205

Leu Asp Gln Leu Arg Lys Arg Val Trp Leu Val Gly Tyr Ala Leu Glu
    210                 215                 220

Glu Met Gly Leu Glu Lys Gly Cys Ala Ile Ala Ile Asp Met Pro Met
225                 230                 235                 240

His Val Asp Ala Val Val Ile Tyr Leu Ala Ile Val Leu Ala Gly Tyr
                245                 250                 255

Val Val Val Ser Ile Ala Asp Ser Phe Ser Ala Pro Glu Ile Ser Thr
            260                 265                 270

Arg Leu Arg Leu Ser Lys Ala Lys Ala Ile Phe Thr Gln Asp His Ile
        275                 280                 285

Ile Arg Gly Lys Lys Arg Ile Pro Leu Tyr Ser Arg Val Val Glu Ala
    290                 295                 300

Lys Ser Pro Met Ala Ile Val Ile Pro Cys Ser Gly Ser Asn Ile Gly
305                 310                 315                 320

Ala Glu Leu Arg Asp Gly Asp Ile Ser Trp Asp Tyr Phe Leu Glu Arg
                325                 330                 335

Ala Lys Glu Phe Lys Asn Cys Glu Phe Thr Ala Arg Glu Gln Pro Val
            340                 345                 350

Asp Ala Tyr Thr Asn Ile Leu Phe Ser Ser Gly Thr Thr Gly Glu Pro
        355                 360                 365

Lys Ala Ile Pro Trp Thr Gln Ala Thr Pro Leu Lys Ala Ala Ala Asp
    370                 375                 380

-continued

```
Gly Trp Ser His Leu Asp Ile Arg Lys Gly Asp Val Ile Val Trp Pro
385                 390                 395                 400

Thr Asn Leu Gly Trp Met Met Gly Pro Trp Leu Val Tyr Ala Ser Leu
            405                 410                 415

Leu Asn Gly Ala Ser Ile Ala Leu Tyr Asn Gly Ser Pro Leu Val Ser
        420                 425                 430

Gly Phe Ala Lys Phe Val Gln Asp Ala Lys Val Thr Met Leu Gly Val
    435                 440                 445

Val Pro Ser Ile Val Arg Ser Trp Lys Ser Thr Asn Cys Val Ser Gly
450                 455                 460

Tyr Asp Trp Ser Thr Ile Arg Cys Phe Ser Ser Gly Glu Ala Ser
465                 470                 475                 480

Asn Val Asp Glu Tyr Leu Trp Leu Met Gly Arg Ala Asn Tyr Lys Pro
                485                 490                 495

Val Ile Glu Met Cys Gly Gly Thr Glu Ile Gly Gly Ala Phe Ser Ala
            500                 505                 510

Gly Ser Phe Leu Gln Ala Gln Ser Leu Ser Ser Phe Ser Ser Gln Cys
        515                 520                 525

Met Gly Cys Thr Leu Tyr Ile Leu Asp Lys Asn Gly Tyr Pro Met Pro
    530                 535                 540

Lys Asn Lys Pro Gly Ile Gly Glu Leu Ala Leu Gly Pro Val Met Phe
545                 550                 555                 560

Gly Ala Ser Lys Thr Leu Leu Asn Gly Asn His Asp Val Tyr Phe
                565                 570                 575

Lys Gly Met Pro Thr Leu Asn Gly Glu Val Leu Arg Arg His Gly Asp
            580                 585                 590

Ile Phe Glu Leu Thr Ser Asn Gly Tyr Tyr His Ala His Gly Arg Ala
        595                 600                 605

Asp Asp Thr Met Asn Ile Gly Gly Ile Lys Ile Ser Ser Ile Glu Ile
    610                 615                 620

Glu Arg Val Cys Asn Glu Val Asp Asp Arg Val Phe Glu Thr Thr Ala
625                 630                 635                 640

Ile Gly Val Pro Pro Leu Gly Gly Gly Pro Glu Gln Leu Val Ile Phe
                645                 650                 655

Phe Val Leu Lys Asp Ser Asn Asp Thr Thr Ile Asp Leu Asn Gln Leu
            660                 665                 670

Arg Leu Ser Phe Asn Leu Gly Leu Gln Lys Lys Leu Asn Pro Leu Phe
        675                 680                 685

Lys Val Thr Arg Val Val Pro Leu Ser Ser Leu Pro Arg Thr Ala Thr
    690                 695                 700

Asn Lys Ile Met Arg Arg Val Leu Arg Gln Gln Phe Ser His Phe Glu
705                 710                 715                 720

<210> SEQ ID NO 4
<211> LENGTH: 385
<212> TYPE: PRT
<213> ORGANISM: Cannabis sativa

<400> SEQUENCE: 4

Met Asn His Leu Arg Ala Glu Gly Pro Ala Ser Val Leu Ala Ile Gly
1               5                   10                  15

Thr Ala Asn Pro Glu Asn Ile Leu Leu Gln Asp Glu Phe Pro Asp Tyr
            20                  25                  30

Tyr Phe Arg Val Thr Lys Ser Glu His Met Thr Gln Leu Lys Glu Lys
        35                  40                  45
```

```
Phe Arg Lys Ile Cys Asp Lys Ser Met Ile Arg Lys Arg Asn Cys Phe
    50                  55                  60

Leu Asn Glu Glu His Leu Lys Gln Asn Pro Arg Leu Val Glu His Glu
65                  70                  75                  80

Met Gln Thr Leu Asp Ala Arg Gln Asp Met Leu Val Val Glu Val Pro
                85                  90                  95

Lys Leu Gly Lys Asp Ala Cys Ala Lys Ala Ile Lys Glu Trp Gly Gln
            100                 105                 110

Pro Lys Ser Lys Ile Thr His Leu Ile Phe Thr Ser Ala Ser Thr Thr
        115                 120                 125

Asp Met Pro Gly Ala Asp Tyr His Cys Ala Lys Leu Leu Gly Leu Ser
130                 135                 140

Pro Ser Val Lys Arg Val Met Met Tyr Gln Leu Gly Cys Tyr Gly Gly
145                 150                 155                 160

Gly Thr Val Leu Arg Ile Ala Lys Asp Ile Ala Glu Asn Asn Lys Gly
                165                 170                 175

Ala Arg Val Leu Ala Val Cys Cys Asp Ile Met Ala Cys Leu Phe Arg
            180                 185                 190

Gly Pro Ser Glu Ser Asp Leu Glu Leu Leu Val Gly Gln Ala Ile Phe
        195                 200                 205

Gly Asp Gly Ala Ala Ala Val Ile Val Gly Ala Glu Pro Asp Glu Ser
210                 215                 220

Val Gly Glu Arg Pro Ile Phe Glu Leu Val Ser Thr Gly Gln Thr Ile
225                 230                 235                 240

Leu Pro Asn Ser Glu Gly Thr Ile Gly Gly His Ile Arg Glu Ala Gly
                245                 250                 255

Leu Ile Phe Asp Leu His Lys Asp Val Pro Met Leu Ile Ser Asn Asn
            260                 265                 270

Ile Glu Lys Cys Leu Ile Glu Ala Phe Thr Pro Ile Gly Ile Ser Asp
        275                 280                 285

Trp Asn Ser Ile Phe Trp Ile Thr His Pro Gly Gly Lys Ala Ile Leu
290                 295                 300

Asp Lys Val Glu Glu Lys Leu His Leu Lys Ser Asp Lys Phe Val Asp
305                 310                 315                 320

Ser Arg His Val Leu Ser Glu His Gly Asn Met Ser Ser Ser Thr Val
                325                 330                 335

Leu Phe Val Met Asp Glu Leu Arg Lys Arg Ser Leu Glu Glu Gly Lys
            340                 345                 350

Ser Thr Thr Gly Asp Gly Phe Glu Trp Gly Val Leu Phe Gly Phe Gly
        355                 360                 365

Pro Gly Leu Thr Val Glu Arg Val Val Arg Ser Val Pro Ile Lys
    370                 375                 380

Tyr
385

<210> SEQ ID NO 5
<211> LENGTH: 101
<212> TYPE: PRT
<213> ORGANISM: Cannabis sativa

<400> SEQUENCE: 5

Met Ala Val Lys His Leu Ile Val Leu Lys Phe Lys Asp Glu Ile Thr
1               5                   10                  15

Glu Ala Gln Lys Glu Glu Phe Phe Lys Thr Tyr Val Asn Leu Val Asn
```

```
            20                  25                  30
Ile Ile Pro Ala Met Lys Asp Val Tyr Trp Gly Lys Asp Val Thr Gln
            35                  40                  45

Lys Asn Lys Glu Glu Gly Tyr Thr His Ile Val Glu Val Thr Phe Glu
         50                  55                  60

Ser Val Glu Thr Ile Gln Asp Tyr Ile Ile His Pro Ala His Val Gly
 65                  70                  75                  80

Phe Gly Asp Val Tyr Arg Ser Phe Trp Glu Lys Leu Leu Ile Phe Asp
                 85                  90                  95

Tyr Thr Pro Arg Lys
            100

<210> SEQ ID NO 6
<211> LENGTH: 99
<212> TYPE: PRT
<213> ORGANISM: Artificial Sequence
<220> FEATURE:
<223> OTHER INFORMATION: synthetic polypeptide sequence lacking the
      N-terminal Met and C-terminal Lys relative to SEQ ID NO:5

<400> SEQUENCE: 6

Ala Val Lys His Leu Ile Val Leu Lys Phe Lys Asp Glu Ile Thr Glu
 1               5                  10                  15

Ala Gln Lys Glu Glu Phe Phe Lys Thr Tyr Val Asn Leu Val Asn Ile
             20                  25                  30

Ile Pro Ala Met Lys Asp Val Tyr Trp Gly Lys Asp Val Thr Gln Lys
         35                  40                  45

Asn Lys Glu Glu Gly Tyr Thr His Ile Val Glu Val Thr Phe Glu Ser
 50                  55                  60

Val Glu Thr Ile Gln Asp Tyr Ile Ile His Pro Ala His Val Gly Phe
 65                  70                  75                  80

Gly Asp Val Tyr Arg Ser Phe Trp Glu Lys Leu Leu Ile Phe Asp Tyr
                 85                  90                  95

Thr Pro Arg

<210> SEQ ID NO 7
<211> LENGTH: 95
<212> TYPE: PRT
<213> ORGANISM: Artificial Sequence
<220> FEATURE:
<223> OTHER INFORMATION: synthetic polypeptide - truncated SEQ ID NO:5
      lacking N-terminal Met and C-terminal YTPRK

<400> SEQUENCE: 7

Ala Val Lys His Leu Ile Val Leu Lys Phe Lys Asp Glu Ile Thr Glu
 1               5                  10                  15

Ala Gln Lys Glu Glu Phe Phe Lys Thr Tyr Val Asn Leu Val Asn Ile
             20                  25                  30

Ile Pro Ala Met Lys Asp Val Tyr Trp Gly Lys Asp Val Thr Gln Lys
         35                  40                  45

Asn Lys Glu Glu Gly Tyr Thr His Ile Val Glu Val Thr Phe Glu Ser
 50                  55                  60

Val Glu Thr Ile Gln Asp Tyr Ile Ile His Pro Ala His Val Gly Phe
 65                  70                  75                  80

Gly Asp Val Tyr Arg Ser Phe Trp Glu Lys Leu Leu Ile Phe Asp
                 85                  90                  95

<210> SEQ ID NO 8
```

-continued

<211> LENGTH: 415
<212> TYPE: PRT
<213> ORGANISM: Ralstonia solanacearum

<400> SEQUENCE: 8

```
Met Ala Phe Asn Glu Arg Val Val Asp Trp Gln Gln Val Ala Gly Ala
1               5                   10                  15

Gln Pro Asp Ala Ser Pro Glu Arg Met Ser Ala Asp Asp Pro Phe Met
            20                  25                  30

Ile Ile Tyr Thr Ser Gly Thr Thr Gly Lys Pro Lys Gly Thr Val His
        35                  40                  45

Thr His Gly Ser Phe Pro Met Lys Ile Ala His Asp Ser Ala Ile His
    50                  55                  60

Phe Asn Val Ser Pro Lys Asp Val Phe Cys Trp Pro Ala Asp Met Gly
65                  70                  75                  80

Trp Val Ala Gly Thr Leu Val Met Ser Cys Ala Leu Leu Arg Gly Ala
                85                  90                  95

Thr Leu Val Cys Tyr Asp Gly Ala Pro Asp Phe Pro Asp Trp Ser Arg
            100                 105                 110

Met Ser Arg Leu Ile Glu Arg His Arg Val Thr His Phe Gly Ser Ala
        115                 120                 125

Pro Thr Leu Ile Arg Gly Leu Ala Ser Asn Glu Ala Ile Ala Thr Gln
    130                 135                 140

Gly Asp Val Ser Ser Val Lys Leu Leu Ile Thr Ala Gly Glu Gly Ile
145                 150                 155                 160

Asp Pro Glu His Phe Leu Trp Phe Gln Lys Ala Phe Gly Gly Gly His
                165                 170                 175

Arg Pro Val Ile Asn Tyr Thr Gly Gly Thr Glu Val Ser Gly Ala Leu
            180                 185                 190

Leu Ser Ser Val Val Ile Lys Pro Ile Ser Pro Ala Gly Phe Asn Thr
        195                 200                 205

Ala Ser Pro Gly Val Ala Thr Asp Val Val Asp Ala Glu Gly His Ser
    210                 215                 220

Val Thr Gly Glu Val Gly Glu Leu Ala Ile Arg Lys Pro Phe Ile Gly
225                 230                 235                 240

Met Thr Arg Ser Phe Trp Gln Asp Asp Glu Arg Tyr Leu Asp Ser Tyr
                245                 250                 255

Trp Arg Thr Ile Pro Gly Ile Trp Val His Gly Asp Leu Ala Met Arg
            260                 265                 270

Arg Glu Asp Gly Met Trp Phe Met Met Gly Arg Ser Asp Asp Thr Ile
        275                 280                 285

Lys Leu Ala Gly Lys Arg Leu Gly Pro Ala Glu Ile Glu Asp Val Leu
    290                 295                 300

Leu Glu Leu Pro Glu Ile Ala Glu Ala Ala Ala Ile Gly Val Glu Asp
305                 310                 315                 320

Pro Val Lys Gly Gln Lys Leu Val Val Phe Val Val Ala Ser Lys Ala
                325                 330                 335

Ser Thr Ala Ser Ala Asp Ala Leu Ala Ser Val Ile Gly Lys His Val
            340                 345                 350

Asp Leu Arg Leu Gly Arg Pro Phe Arg Pro Ser Val Val His Val Val
        355                 360                 365

Ala Gln Leu Pro Lys Thr Arg Ser Ser Lys Ile Met Arg Arg Val Ile
    370                 375                 380

Arg Ser Val Tyr Thr Gly Lys Pro Ala Gly Asp Leu Ser Ser Leu Asp
```

```
                385                 390                 395                 400

Asn Pro Leu Ala Leu Asp Glu Ile Arg Ser Ala Ala Ala Val Ser
                    405                 410                 415

<210> SEQ ID NO 9
<211> LENGTH: 12
<212> TYPE: PRT
<213> ORGANISM: Artificial Sequence
<220> FEATURE:
<223> OTHER INFORMATION: synthetic AMP-binding motif
<220> FEATURE:
<221> NAME/KEY: MISC_FEATURE
<222> LOCATION: (1)..(1)
<223> OTHER INFORMATION: Xaa is Leu, Iso, Val, Met, Phe, or Tyr
<220> FEATURE:
<221> NAME/KEY: MISC_FEATURE
<222> LOCATION: (2)..(2)
<223> OTHER INFORMATION: Xaa is any amino acid except Glu
<220> FEATURE:
<221> NAME/KEY: MISC_FEATURE
<222> LOCATION: (3)..(3)
<223> OTHER INFORMATION: Xaa is any amino acid except Val, Glu, and Ser
<220> FEATURE:
<221> NAME/KEY: MISC_FEATURE
<222> LOCATION: (4)..(4)
<223> OTHER INFORMATION: Xaa is Ser, Thr, or Gly
<220> FEATURE:
<221> NAME/KEY: MISC_FEATURE
<222> LOCATION: (5)..(5)
<223> OTHER INFORMATION: Xaa is Ser, Thr, Ala, or Gly
<220> FEATURE:
<221> NAME/KEY: MISC_FEATURE
<222> LOCATION: (7)..(7)
<223> OTHER INFORMATION: Xaa is Ser or Thr
<220> FEATURE:
<221> NAME/KEY: MISC_FEATURE
<222> LOCATION: (8)..(8)
<223> OTHER INFORMATION: Xaa is Ser, Thr, Iso, or Glu
<220> FEATURE:
<221> NAME/KEY: MISC_FEATURE
<222> LOCATION: (9)..(9)
<223> OTHER INFORMATION: Xaa is Ser or Gly
<220> FEATURE:
<221> NAME/KEY: MISC_FEATURE
<222> LOCATION: (10)..(10)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Pro, Ala, Ser, Leu, Iso, Val or Met
<220> FEATURE:
<221> NAME/KEY: MISC_FEATURE
<222> LOCATION: (12)..(12)
<223> OTHER INFORMATION: Xaa is Lys or Arg

<400> SEQUENCE: 9

Xaa Xaa Xaa Xaa Xaa Gly Xaa Xaa Xaa Xaa Xaa Xaa
1               5                   10
```